US010584376B2

(12) United States Patent
Shaffer et al.

(10) Patent No.: US 10,584,376 B2
(45) Date of Patent: Mar. 10, 2020

(54) COMPOSITIONS AND METHODS FOR DETECTING A NUCLEIC ACID SEQUENCE IN A SAMPLE COMPRISING A PRIMER OLIGONUCLEOTIDE WITH A 3'-TERMINAL REGION COMPRISING A 2'-MODIFIED NUCLEOTIDE

(71) Applicant: ENVIROLOGIX INC., Portland, ME (US)

(72) Inventors: Daniel Shaffer, Portland, ME (US); Stephen A. Judice, Portland, ME (US)

(73) Assignee: ENVIROLOGIX INC., Portland, ME (US)

( * ) Notice: Subject to any disclaimer, the term of this patent is extended or adjusted under 35 U.S.C. 154(b) by 0 days.

(21) Appl. No.: 16/117,949

(22) Filed: Aug. 30, 2018

(65) Prior Publication Data

US 2018/0363046 A1    Dec. 20, 2018

Related U.S. Application Data

(63) Continuation of application No. 15/808,442, filed on Nov. 9, 2017, now Pat. No. 10,077,467, which is a continuation of application No. 15/438,330, filed on Feb. 21, 2017, now abandoned, which is a continuation of application No. 14/989,687, filed on Jan. 6, 2016, now Pat. No. 9,631,231, which is a continuation of application No. 14/789,545, filed on Jul. 1, 2015, now Pat. No. 9,322,053, which is a continuation of application No. 14/342,766, filed as application No. PCT/US2013/035750 on Apr. 9, 2013, now Pat. No. 9,096,897.

(60) Provisional application No. 61/621,975, filed on Apr. 9, 2012.

(51) Int. Cl.
| *C12Q 1/6853* | (2018.01) |
| *C12Q 1/6848* | (2018.01) |
| *C12Q 1/689* | (2018.01) |
| *C12Q 1/6851* | (2018.01) |
| *C12Q 1/68* | (2018.01) |

(52) U.S. Cl.
CPC ......... *C12Q 1/6853* (2013.01); *C12Q 1/6848* (2013.01); *C12Q 1/68* (2013.01); *C12Q 1/689* (2013.01); *C12Q 1/6851* (2013.01)

(58) Field of Classification Search
None
See application file for complete search history.

(56) References Cited

U.S. PATENT DOCUMENTS

| 5,952,202 A | 9/1999 | Aoyagi et al. |
| 6,063,604 A | 5/2000 | Wick et al. |
| 6,130,038 A | 10/2000 | Becker et al. |
| 6,355,421 B1 | 3/2002 | Coull |
| 6,794,142 B2 | 9/2004 | Laird et al. |
| 6,977,148 B2 | 12/2005 | Dean et al. |
| 7,056,671 B2 | 6/2006 | Enoki et al. |
| 7,074,600 B2 | 7/2006 | Dean et al. |
| 7,112,423 B2 | 9/2006 | Van Ness et al. |
| 9,096,897 B2 | 8/2015 | Shaffer et al. |
| 9,322,053 B2 | 4/2016 | Shaffer et al. |
| 2003/0060431 A1 | 3/2003 | Simmonds et al. |
| 2005/0059003 A1 | 3/2005 | Enoki et al. |
| 2007/0054296 A1 | 3/2007 | Piepenburg et al. |
| 2008/0274458 A1 | 11/2008 | Latham et al. |
| 2009/0017453 A1 | 1/2009 | Maples et al. |
| 2009/0081670 A1 | 3/2009 | Maples et al. |
| 2009/0197254 A1 | 8/2009 | Lee |
| 2013/0280706 A1 | 10/2013 | Judice |

FOREIGN PATENT DOCUMENTS

| CN | 1633505 A | 6/2005 |
| EP | 1201768 | 5/2002 |
| EP | 1420069 | 5/2004 |
| EP | 2836609 | 2/2015 |
| JP | 2002-291490 | 10/2002 |
| JP | 2004-532615 | 10/2004 |
| JP | 2008-526228 | 7/2008 |
| JP | 2011521624 A | 11/2009 |
| JP | 2010-533494 | 10/2010 |
| JP | 2011-521624 | 7/2011 |
| KR | 10-2004-0028991 | 4/2004 |
| WO | 2002/057479 | 7/2002 |
| WO | 2003/008622 A2 | 1/2003 |
| WO | 2003008622 A2 | 1/2003 |
| WO | 2003-016569 | 2/2003 |
| WO | 2006/074162 | 7/2006 |
| WO | 2008/002920 A2 | 1/2008 |
| WO | 2008022920 A2 | 1/2008 |

(Continued)

OTHER PUBLICATIONS

English translation of Japanese Office Action for corresponding JP 2015-505849, dated Mar. 31, 2015 (2 pages).

(Continued)

*Primary Examiner* — Kenneth R Horlick

(74) *Attorney, Agent, or Firm* — Melissa Hunter-Ensor; Jana E. Harris; Greenberg Traurig, LLP

(57) ABSTRACT

The present invention features compositions and methods for quantifying detection of a target oligonucleotide in a sample in real time comprising one or more primer oligonucleotides comprising a 5' nicking enzyme recognition site and a 3'-terminal region comprising a 2'-modified nucleotide. These methods are compatible with amplification of target oligonucleotides in a test sample, including biological samples, using a nicking amplification reaction.

13 Claims, 12 Drawing Sheets

Specification includes a Sequence Listing.

(56) References Cited

FOREIGN PATENT DOCUMENTS

| WO | 2009/012246 A2 | 1/2009 |
| WO | 2009012246 A2 | 1/2009 |
| WO | 2009/135093 A2 | 11/2009 |
| WO | 2009135093 | 11/2009 |
| WO | 2012/021493 | 2/2012 |
| WO | 2012/021493 A3 | 2/2012 |
| WO | 2012/022755 A1 | 2/2012 |
| WO | 2012021493 A2 | 2/2012 |
| WO | 2012022755 A | 2/2012 |
| WO | 2013155056 | 10/2013 |

OTHER PUBLICATIONS

Canadian Office Action and Examination Report for corresponding Canadian Patent Application No. 2,869,971, dated Dec. 4, 2014 (6 pages).
Holland et al., "Detection of specific polymerase chain reaction product by utilizing the 5' → 3' exonuclease activity of Thermus aquaticus DNA polymerase," Proc. Natl. Acad. Sci., USA, vol. 88, pp. 7276-7280 (Aug. 1991).
International Search Report and Written Opinion, for corresponding PCT/US2011/047049, dated Mar. 16, 2012, 11 pages.
Korean Office Action for corresponding Korean Patent Application No. 10-2014-7031343, dated Mar. 23, 2015 (2 pages).
International Search Report PCT/US2013/035750, dated Oct. 17, 2013.
Notomi et al., "Loop-mediated Isotermal Amplification of DNA," Nucleic Acids Research, vol. 29. No. 12, Oxford University Press (2000).
English Translation of Office Action issued in corresponding Chinese Patent Application No. 201380029891.7, dated Oct. 23, 2015 (9 pages).
Office Action issued in corresponding New Zealand Patent Application No. 701145, dated Sep. 28, 2015 (3 pages).
Office Action issued in corresponding Canadian Patent Application No. 2,869,971, dated Jul. 15, 2015 (5 pages).
Australian Office Action issued in Australian Application No. 2015246059 dated Nov. 21, 2016.
Canadian Office Action issue in Canadian Application No. 2,869,971 dated Oct. 28, 2016.
Craw et al., "Isothermic nucleic acid amplification technologies for point-of-care diagnostics: a critical review", Lab Chip, 2012, vol. 12, pp. 2469-2486.
Li et al., "Enzymatic signal amplification of molecular beacons for sensitive DNA detection," Nucleic Acids Research, 2008, vol. 36, No. 6, e36, pp. 1-17.
English Translation of Japanese Office Action for corresponding Japanese Application No. 2015-166615 dated Jun. 22, 2016.
European Search Report issued in European Application No. 13775206 dated Oct. 8, 2015.
Office Action issued in corresponding New Zealand Application No. 701145, dated May 24, 2016.
English Translation of Third Office Action for corresponding Chinese Patent Application No. 201380029891.7, dated Feb. 4, 2017 (9 pages).
Examination report for corresponding European Patent Application No. 13775206.9, dated Apr. 25, 2017 (5 pages).
Examination Report in corresponding New Zealand Patent Application No. 723570, dated May 23, 2017 (5 pages).
Translation of Office Action issued in corresponding Japanese Patent Application No. JP 2016-164716, dated Aug. 1, 2016 (6 pages).
Translation of Decision on Rejection for corresponding Chinese Application No. 2013800298917, dated Sep. 5, 2017.
U.S. Appl. No. 15/808,442, filed Nov. 9, 2017.
English translation of Japanese Office Action issued in corresponding Japanese Application No. JP 2017-125772, dated May 29, 2018 (2 pages).
New Zealand Examination Report issued in corresponding New Zealand Application 723570, dated Apr. 13, 2018 (3 pages).
English Translation of Korean Office Action issued in corresponding Korean Application No. 10-2015-7016789, dated May 9, 2018 (3 pages).
European Office Action issued in corresponding European application 13 775 206.9, dated May 2, 2018. (4 pages).
English Translation of Korean Office Action issued in corresponding Korean Application No. 10-2015-7016789, dated Dec. 28, 2018 (2 pages).
First Examination Report for corresponding Australian Patent Application No. 2018201671, dated Jul. 25, 2019 (2 pages).
Office Action for corresponding Indian Patent Application No. 8831/DELNP/2014, dated Aug. 22 (8 pages).
Office Action for corresponding Brazil Patent Application No. BR1120140252629, dated Aug. 12, 2019 (4 pages).
English Translation of Office Action for corresponding Brazil Patent Application No. BR1120140252629, dated Aug. 12, 2019 (4 pages).
Extended European Search Report in corresponding European Patent Application No. 19175608.9, dated Nov. 28, 2019 (9 pages).

FIG. 1

Exemplary polymerase-arresting entity structures.

Example positions of a single 2'-o-Methyl RNA base:
5'-TGACTCCATATGGAGTC*ACAT*mGGTTCATTCGTG-3'
5'-TGACTCCATATGGAGTC*ACAT*GmGTTCATTCGTG-3'
5'-TGACTCCATATGGAGTC*ACAT*GGmUTCATTCGTG-3'
5'-TGACTCCATATGGAGTC*ACAT*GGTmUCATTCGTG-3'
5'-TGACTCCATATGGAGTC*ACAT*GGTTmCATTCGTG-3'
5'-TGACTCCATATGGAGTC*ACAT*GGTTCmATTCGTG-3'
5'-TGACTCCATATGGAGTC*ACAT*GGTTCAmUTCGTG-3'
5'-TGACTCCATATGGAGTC*ACAT*GGTTCATmUCGTG-3'
5'-TGACTCCATATGGAGTC*ACAT*GGTTCATTmCGTG-3'
5'-TGACTCCATATGGAGTC*ACAT*GGTTCATTCmGTG-3'
5'-TGACTCCATATGGAGTC*ACAT*GGTTCATTCGmUG-3'
5'-TGACTCCATATGGAGTC*ACAT*GGTTCATTCGTmG-3'

Example positions of a block of two contiguous 2'-o-Methyl RNA bases:
5'-TGACTCCATATGGAGTC*ACAT*mGmGTTCATTCGTG-3'
5'-TGACTCCATATGGAGTC*ACAT*GmGmUTCATTCGTG-3'
5'-TGACTCCATATGGAGTC*ACAT*GGmUmUCATTCGTG-3'
5'-TGACTCCATATGGAGTC*ACAT*GGTmUmCATTCGTG-3'
5'-TGACTCCATATGGAGTC*ACAT*GGTTmCmATTCGTG-3'
5'-TGACTCCATATGGAGTC*ACAT*GGTTCmAmUTCGTG-3'
5'-TGACTCCATATGGAGTC*ACAT*GGTTCAmUmUCGTG-3'
5'-TGACTCCATATGGAGTC*ACAT*GGTTCATmUmGGTG-3'
5'-TGACTCCATATGGAGTC*ACAT*GGTTCATTmCmGTG-3'
5'-TGACTCCATATGGAGTC*ACAT*GGTTCATTCmGmUG-3'
5'-TGACTCCATATGGAGTC*ACAT*GGTTCATTCGmUmG-3'

FIG. 1 continued

Example positions of a block of three contiguous 2'-o-Methyl RNA bases:
```
5'-TGACTCCATATGGAGTCACAT mGmGmUTCATTCGTG -3'
5'-TGACTCCATATGGAGTCACAT GmGmUmUCATTCGTG -3'
5'-TGACTCCATATGGAGTCACAT GGmUmUmCATTCGTG -3'
5'-TGACTCCATATGGAGTCACAT GGTmUmCmATTCGTG -3'
5'-TGACTCCATATGGAGTCACAT GGTTmCmAmUTCGTG -3'
5'-TGACTCCATATGGAGTCACAT GGTTCmAmUmUCGTG -3'
5'-TGACTCCATATGGAGTCACAT GGTTCAmUmUmCGTG -3'
5'-TGACTCCATATGGAGTCACAT GGTTCATmUmCmGTG -3'
5'-TGACTCCATATGGAGTCACAT GGTTCATTmCmGmUG -3'
5'-TGACTCCATATGGAGTCACAT GGTTCATTCmGmUmG -3'
```

Example positions of a block of four contiguous 2'-o-Methyl RNA bases:
```
5'-TGACTCCATATGGAGTCACAT mGmGmUmUCATTCGTG -3'
5'-TGACTCCATATGGAGTCACAT GmGmUmUmCATTCGTG -3'
5'-TGACTCCATATGGAGTCACAT GGmUmUmCmATTCGTG -3'
5'-TGACTCCATATGGAGTCACAT GGTmUmCmAmUTCGTG -3'
5'-TGACTCCATATGGAGTCACAT GGTTmCmAmUmUCGTG -3'
5'-TGACTCCATATGGAGTCACAT GGTTCmAmUmUmCGTG -3'
5'-TGACTCCATATGGAGTCACAT GGTTCAmUmUmCmGTG -3'
5'-TGACTCCATATGGAGTCACAT GGTTCATmUmCmGmUG -3'
5'-TGACTCCATATGGAGTCACAT GGTTCATTmCmGmUmG -3'
```

FIG. 1 continued

Example positions of a block of five contiguous 2'-o-Methyl RNA bases:

5'-TGACTCCATATGGAGTC*ACAT*mGmGmUmUmCATTCGTG-3'
5'-TGACTCCATATGGAGTC*ACAT*GmGmUmUmCmATTCGTG-3'
5'-TGACTCCATATGGAGTC*ACAT*GGmUmUmCmAmUTCGTG-3'
5'-TGACTCCATATGGAGTC*ACAT*GGTmUmCmAmUmUCGTG-3'
5'-TGACTCCATATGGAGTC*ACAT*GGTTmCmAmUmUmCGTG-3'
5'-TGACTCCATATGGAGTC*ACAT*GGTTCmAmUmUmCmGTG-3'
5'-TGACTCCATATGGAGTC*ACAT*GGTTCAmUmUmCmGmUG-3'
5'-TGACTCCATATGGAGTC*ACAT*GGTTCATmUmCmGmUmG-3'

Example positions of a completely contiguous 2'-o-Methyl RNA bases:

5'-TGACTCCATATGGAGTC*ACAT*mGmGmUmUmCmAmUmUmCmGmUmG-3'
5'-TGACTCCATATGGAGTC*ACAT*GmGmUmUmCmAmUmUmCmGmUmG-3'
5'-TGACTCCATATGGAGTC*ACAT*GGmUmUmCmAmUmUmCmGmUmG-3'
5'-TGACTCCATATGGAGTC*ACAT*GGTmUmCmAmUmUmCmGmUmG-3'
5'-TGACTCCATATGGAGTC*ACAT*GGTTmCmAmUmUmCmGmUmG-3'
5'-TGACTCCATATGGAGTC*ACAT*GGTTCmAmUmUmCmGmUmG-3'
5'-TGACTCCATATGGAGTC*ACAT*GGTTCAmUmUmCmGmUmG-3'
5'-TGACTCCATATGGAGTC*ACAT*GGTTCATmUmCmGmUmG-3'
5'-TGACTCCATATGGAGTC*ACAT*GGTTCATTmCmGmUmG-3'
5'-TGACTCCATATGGAGTC*ACAT*GGTTCATTCmGmUmG-3'
5'-TGACTCCATATGGAGTC*ACAT*GGTTCATTCGmUmG-3'
5'-TGACTCCATATGGAGTC*ACAT*GGTTCATTCGTmG-3'

Key:
Black = Stabilizer sequence
Blue = Nicking Enzyme Recognition Sequence
*Green* = Nicking Enzyme Spacer Sequence
Red = Target Specific Recognition Sequence
mX = 2'-o-Methyl RNA base
A = Adenine
T = Thymine
G = Guanine
C = Cystosine
U = Uracil
Underlined base(s) delineates the modified sequence segment

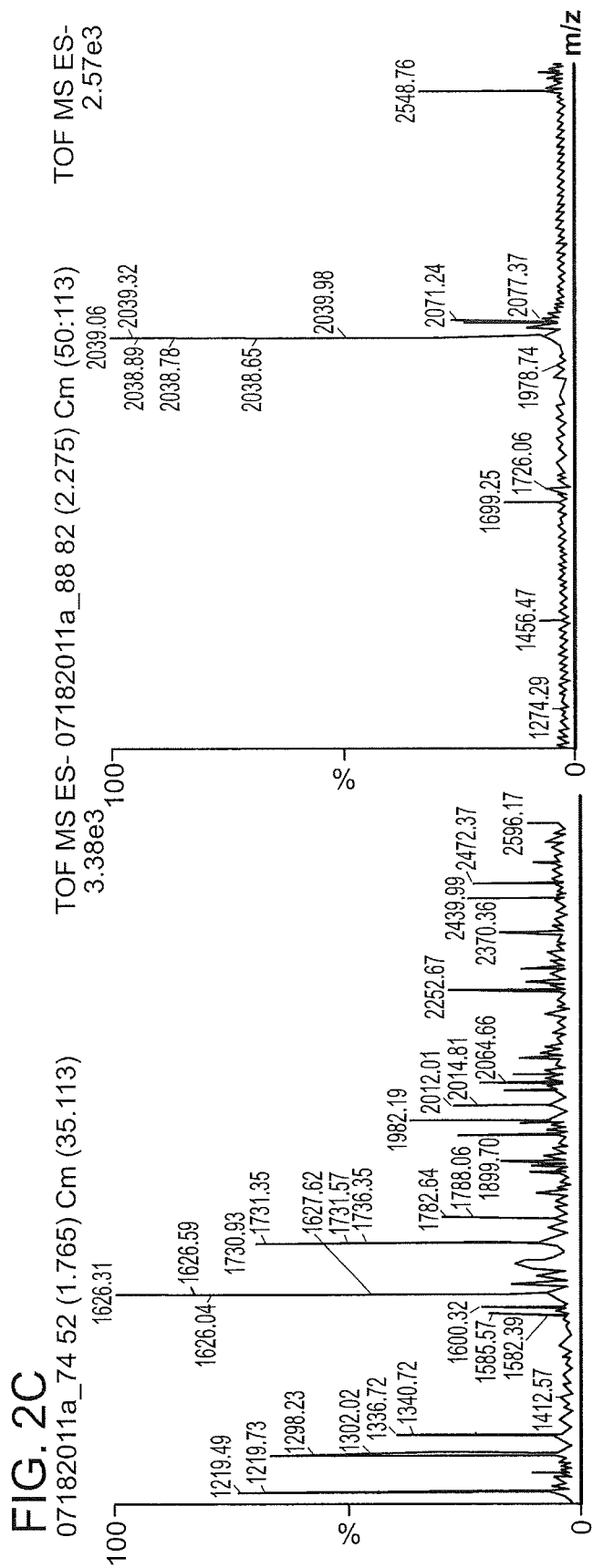

FIG. 7

TS3 set of forward & reverse template-primer:

Forward: 5'-cgcggagtcctcg AACT $_{[MeO]}$A T $_{[MeO]}$A T $_{[MeO]}$GC $_{[MeO]}$C $_{[MeO]}$A $_{[MeO]}$C $_{[MeO]}$G $_{[MeO]}$CA-3'
Reverse: 5'-cgcggagtccgcg TGTAC $_{[MeO]}$A G $_{[MeO]}$C T $_{[MeO]}$CC $_{[MeO]}$AC $_{[MeO]}$C $_{[MeO]}$A $_{[MeO]}$C $_{[MeO]}$A $_{[MeO]}$UT-3'

TS6 set of forward & reverse template-primer:

Forward: 5'-cgcggagtcctcg AACTATAAGC $_{[MeO]}$C $_{[MeO]}$A $_{[MeO]}$C $_{[MeO]}$G $_{[MeO]}$C $_{[MeO]}$A-3'
Reverse: 5'-cgcggagtccgcg TGTACAGTCCAC $_{[MeO]}$C $_{[MeO]}$A $_{[MeO]}$C $_{[MeO]}$A $_{[MeO]}$U $_{[MeO]}$U-3'

FIG. 8

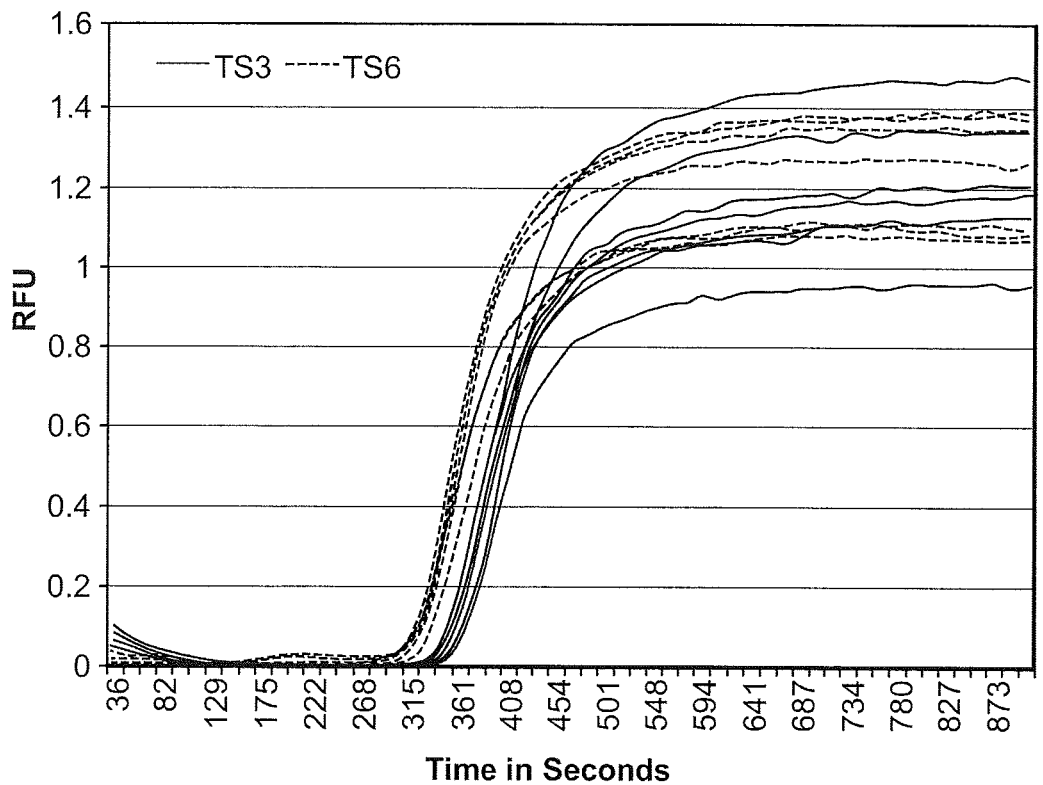

COMPOSITIONS AND METHODS FOR DETECTING A NUCLEIC ACID SEQUENCE IN A SAMPLE COMPRISING A PRIMER OLIGONUCLEOTIDE WITH A 3'-TERMINAL REGION COMPRISING A 2'-MODIFIED NUCLEOTIDE

CROSS-REFERENCE TO RELATED APPLICATIONS

This application is a continuation of U.S. patent application Ser. No. 15/808,442, filed Nov. 9, 2017, now U.S. Pat. No. 10,077,467; which is a continuation of U.S. patent application Ser. No. 15/438,330, filed Feb. 21, 2017, abandoned; which is a continuation of U.S. patent application Ser. No. 14/989,687, filed Jan. 6, 2016, now U.S. Pat. No. 9,631,231, which is a continuation of U.S. patent application Ser. No. 14/789,545, filed Jul. 1, 2015, now U.S. Pat. No. 9,322,053; which is a continuation of U.S. patent application Ser. No. 14/342,766, filed Mar. 4, 2014, now U.S. Pat. No. 9,096,897, which is the U.S. national phase application, pursuant to 35 U.S.C. § 371, of PCT International Application Ser. No. PCT/US2013/035750, filed Apr. 9, 2013, designating the United States and published in English, which claims priority to and the benefit of U.S. Provisional Application No. 61/621,975, filed Apr. 9, 2012; each of the aforementioned applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 28, 2018, is named 167665.010633_SL.txt and is 26,102 bytes in size.

BACKGROUND OF THE INVENTION

Nucleic acid amplification technologies have provided a means of understanding complex biological processes, detection, identification, and quantification of pathogenic and non-pathogenic organisms, forensic criminology analysis, disease association studies, and detection of events in genetically modified organisms, etc. The polymerase chain reaction (PCR) is a common thermal cycling dependent nucleic acid amplification technology used to amplify DNA consisting of cycles of repeated heating and cooling of the reaction for DNA melting and enzymatic replication of the DNA using a DNA polymerase. Real-Time quantitative PCR (qPCR) is a technique used to quantify the number of copies of a given nucleic acid sequence in a biological sample. Currently, qPCR utilizes the detection of reaction products in real-time throughout the reaction and compares the amplification profile to the amplification of controls which contain a known quantity of nucleic acids at the beginning of each reaction (or a known relative ratio of nucleic acids to the unknown tested nucleic acid). The results of the controls are used to construct standard curves, typically based on the logarithmic portion of the standard reaction amplification curves. These values are used to interpolate the quantity of the unknowns based on where their amplification curves compared to the standard control quantities.

In addition to PCR, non-thermal cycling dependent amplification systems or isothermal nucleic acid amplification technologies exist including, without limitation: Nicking and Extension Amplification Reaction (NEAR), Rolling Circle Amplification (RCA), Helicase-Dependent Amplification (HDA), Loop-Mediated Amplification (LAMP), Strand Displacement Amplification (SDA), Transcription-Mediated Amplification (TMA), Self-Sustained Sequence Replication (3SR), Nucleic Acid Sequence Based Amplification (NASBA), Single Primer Isothermal Amplification (SPIA), Q-β Replicase System, and Recombinase Polymerase Amplification (RPA).

NEAR amplification has similarities to PCR thermocycling. Like PCR, NEAR amplification employs oligonucleotide sequences which are complementary to a target sequences referred to as primers in PCR and templates in NEAR. In addition, NEAR amplification of target sequences results in a logarithmic increase in the target sequence, just as it does in standard PCR. Unlike standard PCR, the NEAR reaction progresses isothermally. In standard PCR, the temperature is increased to allow the two strands of DNA to separate. In a NEAR reaction, the target nucleic acid sequence is nicked at specific nicking sites present in a test sample. The polymerase infiltrates the nick site and begins complementary strand synthesis of the nicked target nucleotide sequence (the added exogenous DNA) along with displacement of the existing complimentary DNA strand. The strand displacement replication process obviates the need for increased temperature. At this point, template/primer molecules anneal to the displaced complementary sequence from the added exogenous DNA. The polymerase now extends from the 3' end of the template, creating a complementary strand to the previously displaced strand. The second template/primer oligonucleotide then anneals to the newly synthesized complementary strand and extends making a duplex of DNA which includes the nicking enzyme recognition sequence. This strand is then liable to be nicked with subsequent strand displacement extension by the polymerase, which leads to the production of a duplex of DNA which has nick sites on either side of the original target DNA. Once this is synthesized, the molecule continues to be amplified exponentially through replication of the displaced strands with new template molecules. In addition, amplification also proceeds linearly from each product molecule through the repeated action of the nick translation synthesis at the template introduced nick sites. The result is a very rapid increase in target signal amplification; much more rapid than PCR thermocycling, with amplification results in less than ten minutes.

Quantification has been problematic, however. Optimal performance of a real-time NEAR system depends on the generation and amplification of a specific product. NEAR systems are known to generate significant levels of non-specific background products in addition to the specific product by the reaction enzymes. These background products can serve as amplifiable entities and their generation can out-compete the generation of specific product. While it is possible to design detection probes specific to the desired target (and thus the specific product is detectable in a complex background), significant levels of non-specific background products sequester reaction components that may have otherwise been utilized for the amplification of the specific product. Thus, sequestration of reaction components due to non-specific background product generation results in a reaction that is suboptimal. This is particularly troublesome when the target nucleic acid is initially in very low abundance and where a highly optimized reaction is required for reliable detection of the target. Also, a suboptimal reaction may not represent true quantification of a target nucleic acid even though it is detectable. It would be advantageous to generate optimized NEAR reactions that eliminate the amplification of non-specific background products. Doing so would provide a reaction that is suitable for quantification either by a standard curve based system or relative quantification.

Also, it is common practice to evaluate NEAR reactions using mass spectrometry. High levels of background products can obscure the interpretation of mass spectrometry data. If, for instance, a reaction contains background products, one or more products derived from non-specific amplification (from related yet dissimilar targets), and the specific product, it would be challenging to identify these matrix-derived products from the background products. Elimination of background products leads to a clear determination of the performance/specificity of the particular assay.

Additionally, high levels of background products can impede the optimal amplification of intentionally-duplexed or multiplexed reactions. While multiple, differentially labeled detection probes are compatible with real-time detection, there still exists the problem of reactant limitations due to non-specific product formation. This is particularly true for duplex or multiplex reactions in that these reactions contain more than two templates/primers that can potentially form complex populations of background products. A NEAR reaction system that eliminates the amplification of background products also provides conditions for the detection of intentionally duplexed or multiplexed reactions in real time. It would be highly advantageous to provide a means to eliminate amplifiable background products thus maximizing the potential of generating specific products in NEAR reactions. It would be desirable if a quantitative result could be provided by accurately monitoring the progress of the reaction in real-time.

SUMMARY OF THE INVENTION

As described below, the present invention features compositions and methods for detection of a target oligonucleotide in a sample in real time that reduces or eliminates the generation of background products, allowing for the quantification of the sample target oligonucleotide. These methods are compatible with target oligonucleotides amplified using a NEAR reaction. The invention is based, at least in part, on the discovery that specific products in single-plexed NEAR reactions can be generated without the generation of background products. The reaction compositions and methods provide for relative quantification of unknown test samples, duplexed reactions, and multiplexed reactions, and the creation of standard curves for absolute quantification of unknown test samples.

In one aspect, the invention provides a method of quantifying a specific product in a nicking and extension amplification reaction, the method involving: contacting a target nucleic acid molecule under substantially isothermal conditions with an exonuclease deficient polymerase, two or more primer/template oligonucleotides, each of which specifically binds to a complementary sequence on the target nucleic acid molecule, a nicking enzyme, and a detectable polynucleotide probe, where each of the primer/template oligonucleotides has one or more 2' modified nucleotides in the sequence complementary to the target nucleic acid molecule; generating amplicons having at least a portion of said target nucleic acid molecule; and detecting a signal specific for oligonucleotide probe hybridization to the target nucleic acid molecule or amplicon thereof, where the signal indicates the quantity of the target nucleic acid molecule present in the sample or an amplicon thereof.

In another aspect, the invention provides a method for detecting a plurality of distinct reaction products produced in the course of a single reaction, the method involving: contacting a target nucleic acid molecule under substantially isothermal conditions with an exonuclease deficient polymerase, two or more primer/template oligonucleotides, each of which specifically binds to a complementary sequence on the target nucleic acid molecule, a nicking enzyme, and a detectable polynucleotide probe, where each of the primer/template oligonucleotides has one or more 2' modified nucleotides in the sequence complementary to the target nucleic acid molecule; generating amplicons having at least a portion of said target nucleic acid molecule; and detecting a signal specific for oligonucleotide probe hybridization to the target nucleic acid molecule or amplicon thereof, where the signal indicates the quantity of the target nucleic acid molecule present in the sample or an amplicon thereof.

In a particular aspect, the invention provides a method of quantifying a specific product in a nicking and extension amplification reaction, the method involving: contacting a target nucleic acid molecule under substantially isothermal conditions with an exonuclease deficient polymerase, two primer/template oligonucleotides, each of which specifically binds to a complementary sequence on the target nucleic acid molecule, a nicking enzyme, and a detectable polynucleotide probe, where each of the primer/template oligonucleotides has at least about 5 contiguous 2'-O-methyl modified nucleotides are positioned at or adjacent to the 3' end of the sequence complementary to the target nucleic acid molecule (e.g., the 3' terminus of the oligonucleotide); generating amplicons having at least a portion of said target nucleic acid molecule; and detecting a signal specific for oligonucleotide probe hybridization to the target nucleic acid molecule or amplicon thereof, where the signal indicates the quantity of the target nucleic acid molecule present in the sample or an amplicon thereof.

In one aspect, the invention provides a method for monitoring in real time a nicking and extension amplification reaction, the method involving: contacting a test sample with an exonuclease deficient polymerase, two or more primer/template oligonucleotides, each of which specifically binds to a complementary sequence on the target nucleic acid molecule, a nicking enzyme, and a detectable polynucleotide probe, where each of the primer/template oligonucleotides has one or more 2' modified nucleotides in the sequence complementary to the target nucleic acid molecule under substantially isothermal conditions; generating amplicons having at least a portion of said target nucleic acid molecule; and detecting a signal in real time, thereby quantitating of the target nucleic acid molecule(s).

In another aspect, the invention provides a method for monitoring in real time a target nucleic acid molecule in a NEAR reaction, the method involving: contacting a target nucleic acid molecule under substantially isothermal conditions with an exonuclease deficient polymerase, two or more primer/template oligonucleotides, each of which specifically binds to a complementary sequence on the target nucleic acid molecule, a nicking enzyme, a heteroduplex specific nicking enzyme, and a detectable polynucleotide probe, where each of the primer/template oligonucleotides has one or more 2' modified nucleotides in the sequence complementary to the target nucleic acid molecule; generating amplicons having a target sequence that binds the detectable oligonucleotide probe; and detecting a signal in real time, thereby quantitating the target nucleic acid molecule.

In yet another aspect, the invention provides a method for monitoring in real time a target nucleic acid molecule in a test sample, the method involving: contacting a target nucleic acid molecule under substantially isothermal conditions with a polymerase, two or more primer/template oligonucleotides, each of which specifically binds to a complementary sequence on the target nucleic acid molecule, a nicking enzyme, a repair enzyme or proof reading enzyme, and a detectable polynucleotide probe, where each of the primer/template oligonucleotides has one or more 2' modified nucleotides in the sequence complementary to the target nucleic acid molecule; generating amplicons having a target sequence that binds the detectable oligonucleotide probe; and detecting a signal in real time, thereby quantitating the target nucleic acid molecule.

In still another aspect, the invention provides a kit for detecting a target sequence in a NEAR reaction, the kit containing one or more primer/template oligonucleotides, which specifically binds to a complementary sequence on the target nucleic acid molecule and has one or more 2' modified nucleotides in the sequence complementary to the target nucleic acid molecule, and directions for use of the primer/template oligonucleotide in methods of the invention.

In one aspect, the invention provides an isolated oligonucleotide having, from 5' to 3', a first region, and a second region, where the first region has a nicking enzyme recognition sequence; where the second region has at least 9 or more nucleotides (e.g., 10, 11, 12, 13, 14, 15, 16, 17, 18, 19, 20, 21, 22, 23, 24, 25, 26, 27, 28, 29, 30 or more contiguous nucleotides) that specifically bind a complementary sequence on a target nucleic acid molecule; and where the second region has one or more 2' modified nucleotides. In other embodiments, the isolated oligonucleotide is one set forth in FIG. 1.

In various embodiments of the aspects delineated herein, the oligonucleotide (e.g., primer/template oligonucleotide, isolated oligonucleotide) contains a modified nucleotide, including a 2' modified nucleotide. In various embodiments of any aspect delineated herein, the 2' modification is one or more of a 2'-O-methyl, 2'-methoxyethoxy, 2'-fluoro, 2'-hydroxyl, 2'-allyl, 2'-O-[2-(methylamino)-2-oxoethyl], 4'-thio, 4'-CH$_2$—O-2'-bridge, 4'-(CH$_2$)$_2$—O-2'-bridge, 2'-LNA, 2'-alkyl, and 2'-O-(N-methylcarbamate) or the modified nucleotide contains a base analog. In various embodiments of any aspect delineated herein, one or more 2' modified nucleotides are positioned at or adjacent to the 3' end of the sequence complementary to the target nucleic acid molecule (e.g., the 3' terminus of the oligonucleotide). In other embodiments of any aspect delineated herein, one or more 2' modified nucleotides are positioned at the 5' end of the sequence complementary to the target nucleic acid molecule. In various embodiments of any aspect delineated herein, one or more 2' modified nucleotides positioned at the 5' end of the sequence complementary to the target nucleic acid molecule are separated from the nick site by 1, 2, 3, 4, 5 or more unmodified nucleotides. In various embodiments of any aspect delineated herein, two or more 2' modified nucleotides are contiguous (2, 3, 4, 5, or more). In other embodiments of any aspect delineated herein, two or more 2' modified nucleotides are alternating with unmodified nucleotides. In various embodiments of any aspect delineated herein, the nicking enzyme recognition sequence is 5'-GAGTC-3'. In various embodiments of any aspect delineated herein, 5 contiguous 2'-O-methyl modified nucleotides are positioned at or adjacent to the 3' end of the sequence complementary to the target nucleic acid molecule (e.g., the 3' terminus of the oligonucleotide). In other embodiments of any aspect delineated herein, 5 contiguous 2'-O-methyl modified nucleotides are positioned at the 5' end of the sequence complementary to the target nucleic acid molecule. In other embodiments of any aspect delineated herein, 2 or more 2'-O-methyl modified nucleotides alternating with unmodified nucleotides are positioned at the 5' end of the sequence complementary to the target nucleic acid molecule (i.e. target specific region).

In various embodiments of any aspect delineated herein, the detecting step does not detect an amplicon of a non-target molecule. In various embodiments of any aspect delineated herein, the method is carried out in real time. In certain embodiments of any aspect delineated herein, the step of generating amplicons is carried out in real time (e.g., to determine the quantity of target present in the reaction).

In various embodiments of any aspect delineated herein, the method provides a semi-quantitative and/or quantity threshold method of determining the amount of nucleic acid molecule present in a biological sample prior to amplification. In various embodiments of any aspect delineated herein, positioning one or more 2' modified nucleotides nearer the 5' end of the sequence complementary to the target nucleic acid molecule increases the detection time of amplification. In various embodiments of any aspect delineated herein, the method further involves the use of ratios of primer/template oligonucleotides to provide increased resolution of reaction products resulting from differing quantities of starting target material. It has been found that increasing the ratio of primer/template oligo having one or more 2' modified nucleotides at the 3' end of the recognition sequence to primer/template oligo having one or more 2' modified nucleotides at the 5' end of the recognition sequence contracted the signal curve and shifted the slope of the curve.

In various embodiments of any aspect delineated herein, the method further involves the use of an amplification rate modifier to provide increased resolution of reaction products resulting from differing quantities of starting target material. In various embodiments of any aspect delineated herein, the target nucleic acid molecule is a DNA or RNA nucleic acid molecule. In various embodiments of any aspect delineated herein, the detectable probe is SYBR green or a Molecular Beacon. In various embodiments of any aspect delineated herein, the detectable probe is a non-amplifiable detectable polynucleotide probe having at least about 10 nucleotides that are complementary to a target sequence, a detectable moiety, and a polymerase-arresting molecule, where the polymerase-arresting molecule prevents a polymerase from amplifying the probe under conditions that otherwise support polymerase activity.

In various embodiments of any aspect delineated herein, the test sample contains a pathogen. In various embodiments of any aspect delineated herein, the pathogen is a virus, bacteria, yeast or fungus. In various embodiments of any aspect delineated herein, the test sample is a biological sample. In various embodiments of any aspect delineated herein, the biological sample is a cell, tissue sample, or biological fluid (e.g., urine, semen, vaginal secretion, or stool). In various embodiments of any aspect delineated herein, the test sample is an environmental sample.

The invention provides compositions and methods for detecting a target nucleic acid molecule amplified using a NEAR reaction. Compositions and articles defined by the invention were isolated or otherwise manufactured in connection with the examples provided below. Other features and advantages of the invention will be apparent from the detailed description, and from the claims.

Definitions

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "polymerase-arresting molecule" is meant a moiety associated with a polynucleotide template/primer that prevents or significantly reduces the progression of a polymerase on the polynucleotide template. Preferably, the moiety is incorporated into the polynucleotide. In one preferred embodiment, the moiety prevents the polymerase from progressing on the template.

By "polymerase extension" is meant the forward progression of a polymerase from a accessible 3'-hydroxyl group that incorporates incoming monomers complementary to their opposing nucleotides on a template polynucleotide strand.

By "exonuclease deficient polymerase" is meant a DNA-dependent DNA polymerase and/or RNA-dependent DNA polymerase that is devoid of a 5'-3' exonuclease activity or that has virtually undetectable levels of such activity.

By "nucleotide adduct" is meant a moiety that is bound covalently or otherwise fixed to a standard nucleotide base.

As used herein, the term "detectable polynucleotide probe" refers to any, at least partially single stranded, polynucleotide labeled with a detectable moiety with a sequence region complementary to at least one strand of the target sequence, which releases a detectable signal from the detectable moiety upon binding to the target sequence, whereas signal generation by that detectable moiety does depend on cleavage of the detectable polynucleotuide probe by a non-specific 5'-3' exonuclease activity. An example of a "detectable polynucleotide probe" as used herein is, but is not limited to, a fluorescent molecular beacon probe as described in prior art.

As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, 2' modified ribonucleotides (e.g., 2'-O-methyl ribonucleotides, 2'-F nucleotides).

As used herein, "modified nucleotide" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-alkyl, such as 2'-O-methyl and 2'-methoxyethoxy, 2'-fluoro, 2'-hydroxyl (RNA), 2'-allyl, 2'-O-[2-(methylamino)-2-oxoethyl], 4'-thio, 4'-$CH_2$—O-2'-bridge, 4'-$(CH_2)_2$—O-2'-bridge, 2'-LNA, and 2'-O-(N-methylcarbamate) or those comprising base analogs.

By "base substitution" is meant a substituent of a nucleobase polymer that does not cause significant disruption of the hybridization between complementary nucleotide strands.

By "specific product" is meant a polynucleotide product resulting from the hybridization of template oligonucleotides to a complementary target sequence and subsequent polymerase mediated extension of the target sequence.

By "nicking and extension amplification reaction" is meant alternating cycles of nicking and extension leading to amplification of a polynucleotide of interest.

By "substantially isothermal condition" is meant at a single temperature or within a narrow range of temperatures that does not vary significantly. In one embodiment, a reaction carried out under substantially isothermal conditions is carried out at a temperature that varies by only about 1-5° C. (e.g., varying by 1, 2, 3, 4, or 5 degrees). In another embodiment, the reaction is carried out at a single temperature within the operating parameters of the instrument utilized.

By "nicking enzyme" is meant a polypeptide capable of recognizing and binding to a specific structure in double stranded nucleic acid molecules and breaking a phosphodiester bond between adjoining nucleotides on a single strand upon binding to its recognized specific structure, thereby creating a free 3'-hydroxyl group on the terminal nucleotide upstream of the nick site that can be extended by a exonuclease deficient polymerase.

By "nick site" is meant the position of a "broken" phosphodiester bond in one strand of a double stranded nucleic acid molecule hydrolyzed by a nicking enzyme.

By "amplicon" is meant a polynucleotide or a multitude of polynucleotides generated during the amplification of a polynucleotide of interest. In one example, an amplicon is generated during a polymerase chain reaction.

By "semi-quantitative" is meant providing an estimate of relative quantity based on an internal control.

By "quantity threshold method" is meant providing an estimate of quantity based on either exceeding or not exceeding in quantity a comparative standard.

By "amplification rate modifiers" is meant an agent capable of affecting either the rate of polymerase extension or the rate of single strand nicking by the nicking enzyme, or both.

By "monitoring a reaction" is meant detecting the progress of a reaction. In one embodiment, monitoring reaction progression involves detecting polymerase extension and/or detecting a complete NEAR reaction.

"Detect" refers to identifying the presence, absence or amount of the analyte to be detected.

By "detectable moiety" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "fragment" is meant a portion of a nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 5, 10, 15, 20, 30, 40, 50, 60, 70, 80, 90, or 100 nucleotides.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, "obtaining" as in "obtaining an agent" includes synthesizing, purchasing, or otherwise acquiring the agent.

By "reference" is meant a standard or control condition. As is apparent to one skilled in the art, an appropriate reference is where an element is changed in order to determine the effect of the element.

By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

By "subject" is meant a mammal, including, but not limited to, a human or non-human mammal, such as a bovine, equine, canine, ovine, or feline.

By "target nucleic acid molecule" is meant a polynucleotide to be analyzed. Such polynucleotide may be a sense or antisense strand of the target sequence. The term "target nucleic acid molecule" also refers to amplicons of the original target sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1 depicts exemplary polymerase-arresting entity structures. Black=Stabilizer Sequence, Blue=Nicking Enzyme Recognition Sequence, Green=Nicking Enzyme Spacer Sequence, Red=Target-Specific Recognition Sequence, A=Adenine, T=Thymine, G=Guanine, C=Cytosine, U=Uracil, mX=2'-O-methyl RNA base. Underlined base(s) delineates the modified sequence segment. FIG. 1 discloses SEQ ID NOS 1-57, 50, 42, 33, 23, and 12, respectively, in order of appearance.

FIGS. 2A-2C depicts evaluation of dynamic range synthetic long-mer to *Clavibacter michiganensis sepidonicus* (Cms) target DNA. Exemplary results from the titration of Cms synthetic "long-mer" target and detection via a fluorobeacon are shown. NEAR assay for Cms performed without input target nucleic acid is indicated as No Target Control (NTC). FIG. 2A is a graph showing that the signal in the No Target Controls (NTC's) was suppressed in the 2'-O-methyl modified primer/template-containing reactions. FIG. 2B is a graph showing that the Standard Curve displayed a wide dynamic range using the 2'-O-methyl template reactions. FIG. 2C is a comparison of exemplary mass spectra data showing the elimination of non-specific amplification products in No Target Controls (NTC) of the Cms assay system using 2'-O-methyl modified primers/templates (right panel), as compared to unmodified primers/templates (left panel). To determine the effect of the 2'-O-methyl modified primers/templates on the generation of background products, samples (10 μl) of No Target Control reactions depicted in FIG. 2A were analyzed via HPLC/Mass Spectrometry. Mass spectra data clearly demonstrate in the presence of 2'-O-methyl modified primers/templates the presence of only the expected molecular species was detected and complex background products generated in the presence of unmodified primers/templates were eliminated.

FIG. 3A is a graph showing that significant signal was observed in the No Target Controls (NTC's), indicating background product generation in the absence of target DNA. FIG. 3B is a graph showing that in the 2'-O-methyl modified template-containing reactions signal in the No Target Controls (NTC's) was suppressed.

FIG. 4A is a graph showing that significant signal was observed in the No Target Controls (NTC's), indicating background product generation in the absence of target DNA. FIG. 4B is a graph showing that in the 2'-O-methyl modified template-containing reactions signal in the No Target Controls (NTC's) was suppressed.

FIG. 7 depicts the design of two primer/template sets (TS3 & TS6) used in a NEAR assay to amplify a fragment of the corn ADH1 gene. The target specific region in the sequences of TS3 & TS6 primer/template sets are significantly longer (15-17 bases) than in primer/template sets of typical NEAR assays (9 to 12 bases) in the prior art. In the TS3 primer/template set the block of 5 consecutive 2'-O-methyl modified nucleotides adjacent to the 3'-terminus is preceded by an upstream region of 2'-O-methyl modified nucleotides alternating with unmodified nucleotides starting with a 2'-O-methyl modified nucleotide 5 or 4 nucleotides downstream from the nick site, respectively. In contrast to TS3, there are only five 2'-O-methyl modified nucleotides in each of the primers/templates of the TS6 set, which form a block of consecutive nucleotides adjacent to the unmodified 3'-terminal nucleotide. FIG. 7 discloses SEQ ID NOS 58-61, respectively, in order of appearance.

FIG. 8 shows amplification plots of the ADH1 assay using two sets of primers/templates (TS3 & TS6) recorded in the SYBRGreen dye detection channel.

DETAILED DESCRIPTION OF THE INVENTION

Figure 2A:
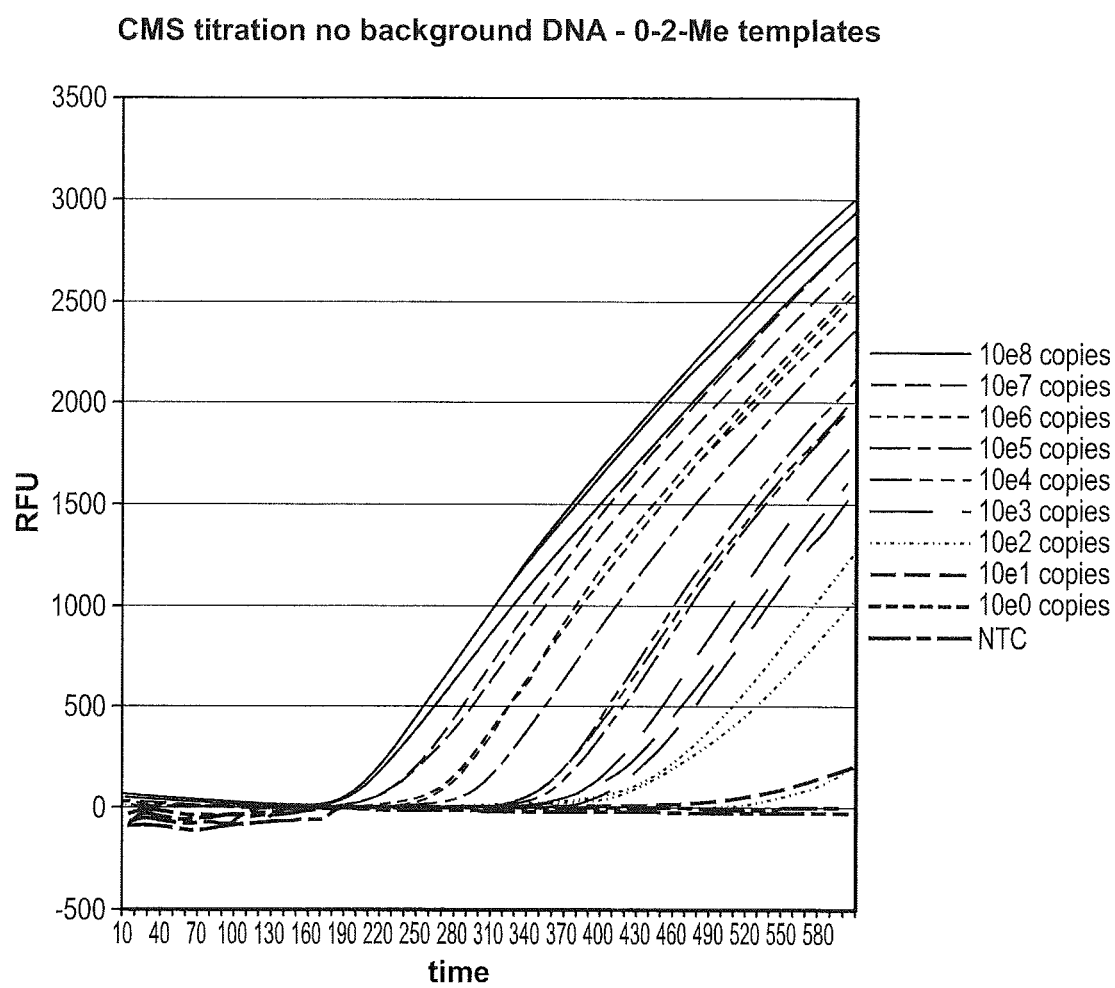
Figure 2B:
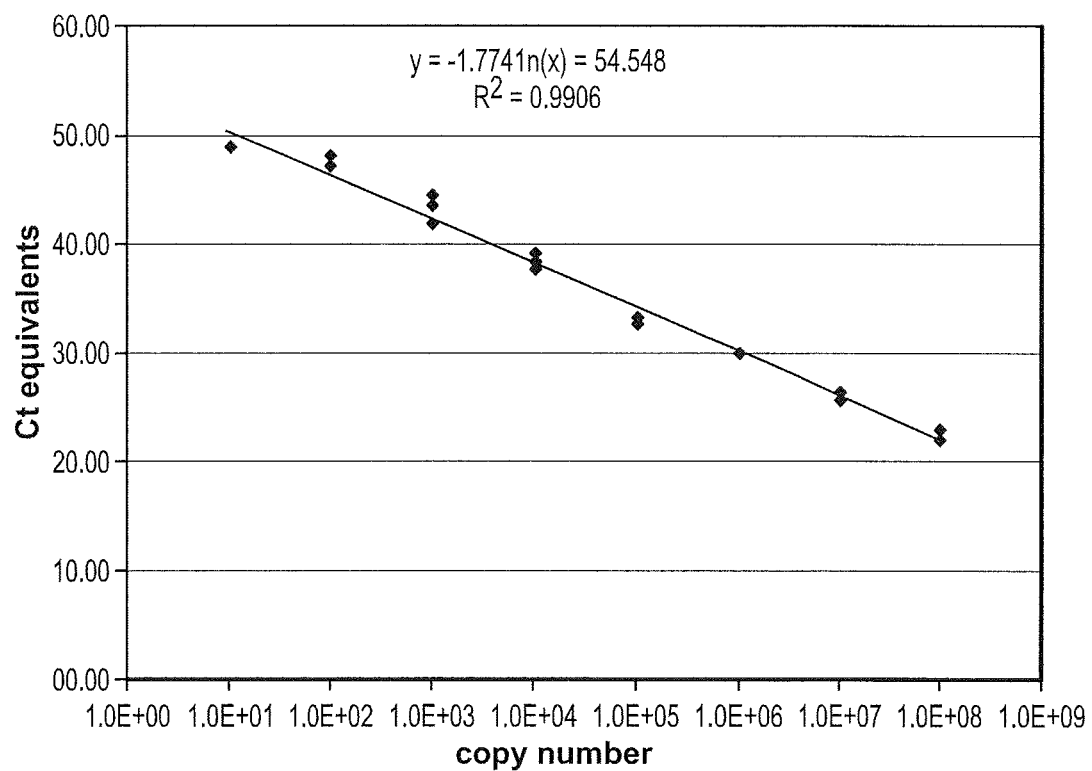
Figure 3:
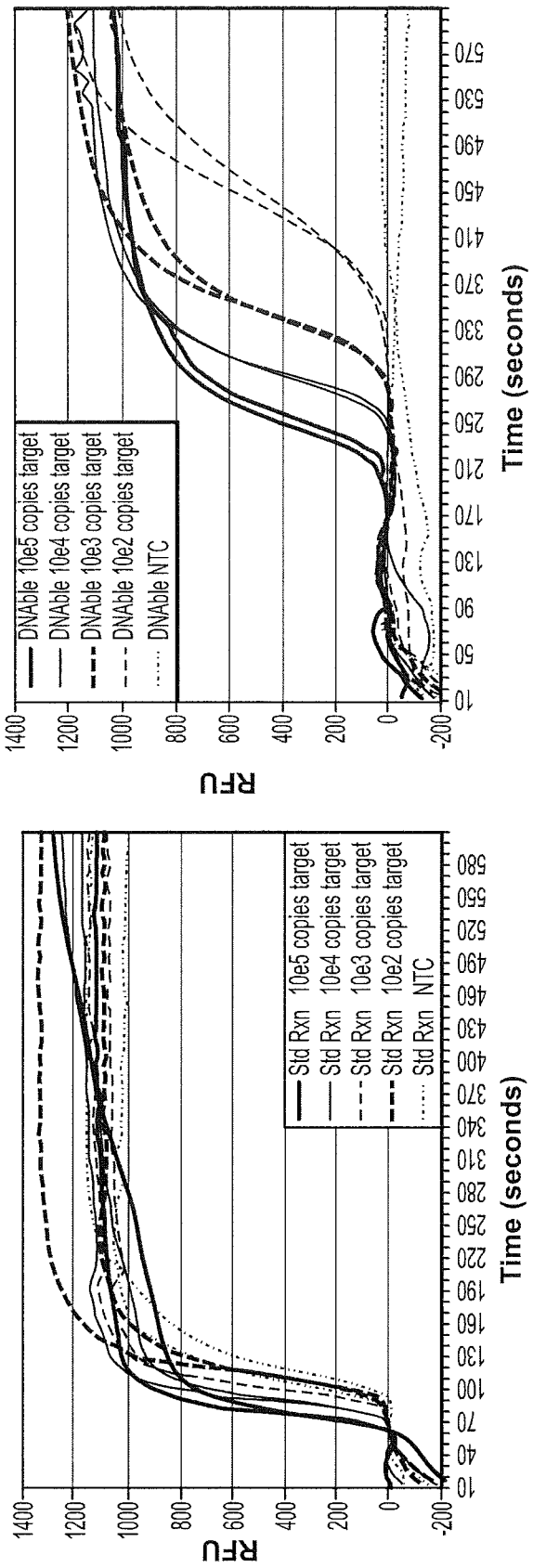
FIG. 3 depicts 2'-O-methyl modification of templates/primers eliminated background signal in NEAR assay using SYBR Green detection. Exemplary amplification data using 2'-O-methyl modified primers/templates and the elimination of non-specific amplification products are shown.
Figure 4:
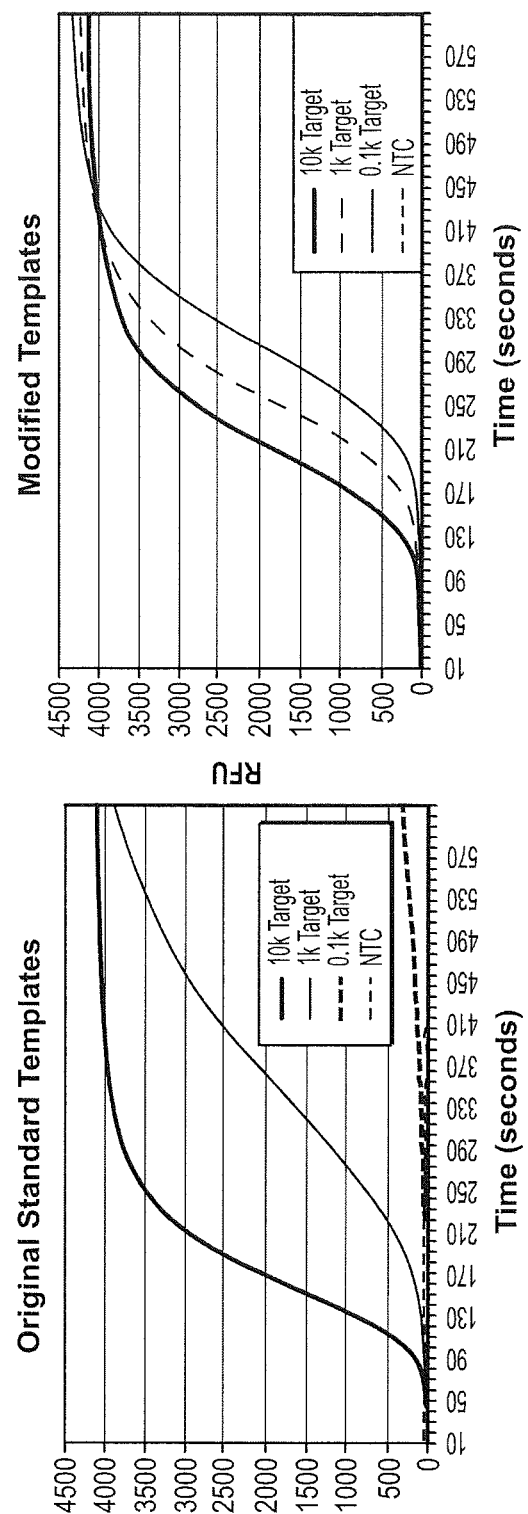
FIG. 4 depicts 2'-O-methyl modification of templates/primers eliminated background signal in NEAR assay using Molecular Beacon detection. Exemplary amplification data using 2'-O-methyl modified primers/templates and the elimination of non-specific amplification products are shown.
Figure 5:
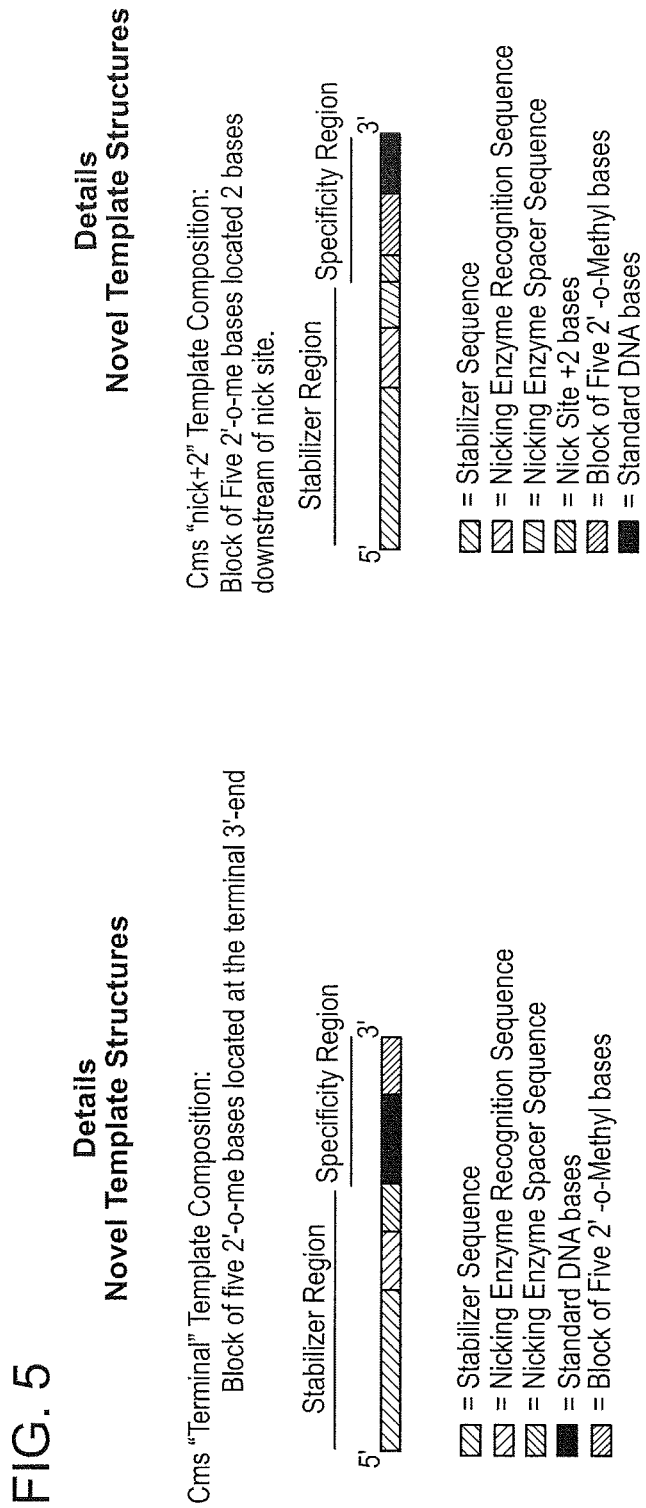
FIG. 5 depicts exemplary polymerase arresting entities using 2'-O-methyl modified primers/templates or ratios of 2'-O-methyl modified primers/templates can be used to manipulate both the time-to-detection and the efficiency of the reaction, thus 'tuning' the reactions. Schematic representations of exemplary 2'-O-methyl modified templates/primers for the tuning of a specific reaction are shown, including a primer/template having a block of five 2'-O-methyl nucleotides at the 3' end ("Terminal" template; left) and a primer/template having a block of five 2'-O-methyl nucleotides starting at the $3^{rd}$ nucleotide after the nick site ("Nick+2" template"; right). Each tuning condition comprises specific ratios of forward and reverse templates with each set of templates having varying structures.
Figure 6:
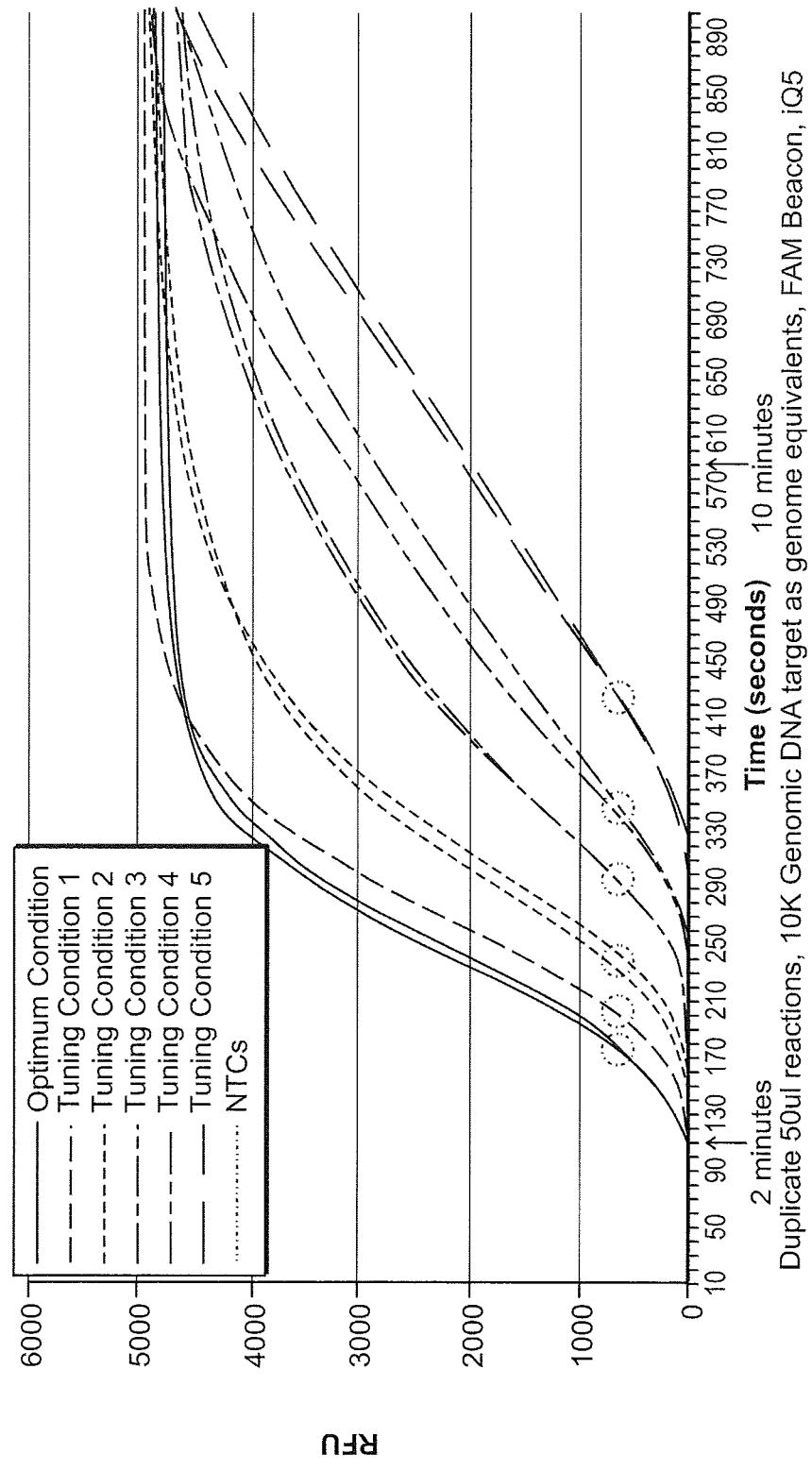
FIG. 6 depicts amplification plots demonstrating the utility of 2'-O-methyl modification of templates/primers for the 'tuning' of a specific reaction. Exemplary amplification data using 2'-O-methyl modified primers/templates are shown. All of the reactions (in duplicate) contained 10,000 genome equivalents of Cms DNA. Each tuning condition represents specific ratios of forward and reverse templates with each set of templates having varying structures. The red circles demonstrate a shift in the time-to-detection for each tuning condition. Additionally, the log phase of each condition was contracted and the slope of the curve was shifted.
Figure 9:
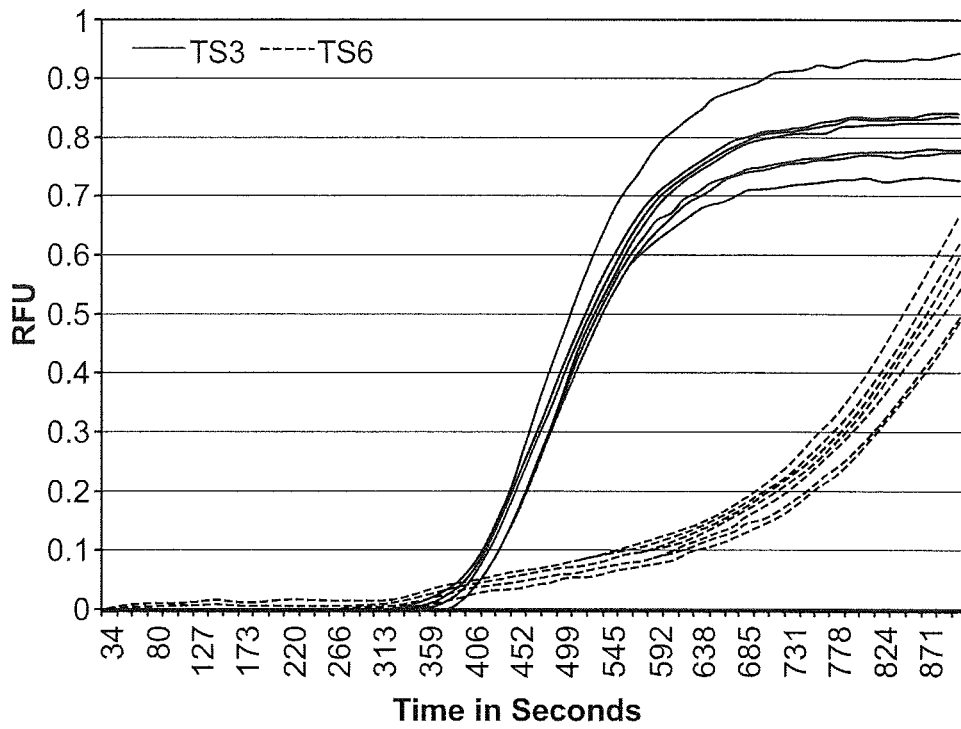
FIG. 9 shows the amplification plots of the same assay reactions recorded in the ROX channel.
Figure 10:
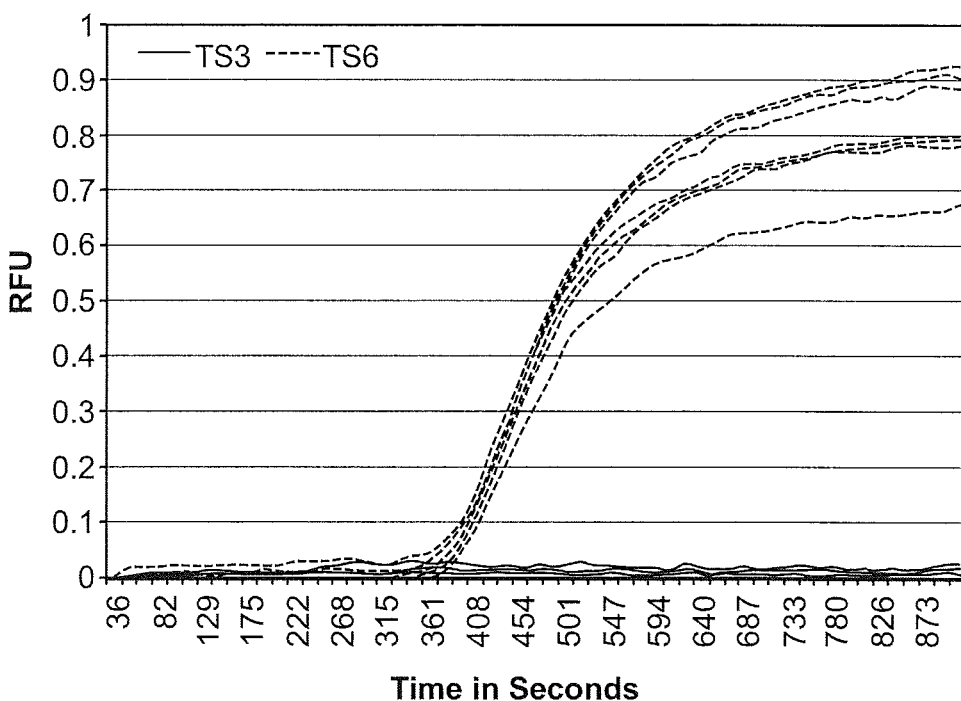
FIG. 10 depicts the amplification plots of the NTC ADH1 assay reactions recorded. Comparing the results shown in FIGS. 8 and 9 it becomes evident that only the primer/template set TS3 produces the ADH1-specific amplicon, while the signal generated by set TS6 is mostly based on non-specific amplification of background products detected only by SYBRgreen.

The invention features compositions and methods that are useful for the quantification of a target nucleic acid molecule in an isothermal reaction. In particular embodiments, the invention provides compositions and methods for the quantification of a target nucleic acid molecule in a NEAR reaction (e.g., in real time).

The invention is based, at least in part, on the surprising discovery that primer-template oligonucleotides comprising a 2' modified (e.g., 2'-O-methyl, 2'-Fluoro) nucleotide reduces or eliminates illegitimate amplification by 5'-3'exonuclease deficient derivatives of Bst DNA polymerase I.
NEAR Reaction.

The NEAR reaction has been used as an endpoint reaction that provides for the non-quantitative detection of target oligonucleotides. The conventional NEAR assay comprises (1) a target nucleic acid molecule; (2) two oligonucleotide molecules that are analagous to the primer molecules of PCR; termed "template-primers" comprising some number of oligonucleotides that are complementary to the target nucleic acid molecule and a site that can be cleaved by a nicking enzyme; (3) dNTPs; (4) a strand displacing, 5'-3'-exonuclease deficient polymerase; and (5) a nicking enzyme. Current methods for quantifying the NEAR reaction, particularly in real time, are inadequate due in part to the illegitimate amplification of non-target molecules present in a sample that can obscure detection of target sequences in a conventional NEAR reaction. For example, there is a consistent undesirable amplification in NEAR reactions that results in a detectable signal in the absence of a target molecule or with signals that do not accurately reflect the amount of target nucleic acid molecule present in the reaction. Although this provides for detection of an endpoint product, it fails to provide for real time monitoring of the reaction.

The present invention provides modified primer/template oligonucleotides that overcome the problem of accurately quantitating a target nucleic acid molecule in a NEAR reaction. It is particularly useful for quantitating a target nucleic acid molecule in a NEAR reaction in real time. The invention is based, at least in part, on the discovery that primer-template oligonucleotides comprising a 2' modified (e.g., 2'-O-methyl, 2'-Fluoro) reduces or eliminates illegitimate amplification without preventing the extension of those modified primer-templates in order to amplifiy the specific product. The primer/template oligonucleotides of the invention are useful in NEAR reactions comprising one or more of the aforementioned NEAR components.

In other embodiments, the invention provides for primer-template oligonucleotides comprising a 2' modified (e.g., 2'-O-methyl, 2'-Fluoro) that is positioned at or adjacent to the 3' terminus of the primer-template. Surprisingly, 2'-O-methyl nucleotides positioned in the 3'-terminal region of a primer-template not only do comprise effective priming substrates for 5'-3'-exonuclease deficient derivatives of Bst DNA polymerase I in isothermal DNA amplification reactions, but use of such modified primer-templates completely suppresses nonspecific primer-dimer amplification. This is particularly surprising because conventional thinking in the field of isothermal DNA amplification teaches that modified nucleotides (e.g., 2'-O-methyl ribonucleotides, unmodified ribonucleotides) could only be introduced at the 5'-terminal region of the primer/template away the 3'-terminus, because placement of 2'-O-methoyl—as well as ribonucleotides within 6 nuleotides from the 3'-terminus of a primer had been demonstrated to inhibit primer extension by DNA polymerases (include as references the patent application from Amersham and the patent from Qiagen). 5'-3' exonuclease deficient derivatives of Bst DNA polymerase I used in NEAR and other isothermal amplification technologies (LAMP) belongs to polA-type bacterial DNA polymerases involved in low synthesis fidelity DNA repair processes. In contrast, high fidelity genome replication in bacteria is catalyzed by DNAE- & POLC type DNA polymerase III holoenzymes, which utilize exclusively RNA primers to initiate DNA replication. In the published prior art the discrimination between RNA and DNA primers was thought to be one mechanism for preventing the interference of high error rate DNA polymerase I enzymes with high fidelity genome replication. In this context the surprising discovery that derivatives of Bst DNA polymerase I can efficiently utilize 2'-modified ribonucleotides as primers for DNA synthesis is remarkable and counterintuitive.

Primer-Template Design

Exemplary polymerase-arresting entity structures from 5' to 3' comprise a stabilizer sequence, nicking enzyme recognition sequence, nicking enzyme spacer sequence, and target specific recognition sequence, the target specific recognition sequence comprising one or more 2' modified nucleotides (e.g., 2'-O-methyl, 2'-methoxyethoxy, 2'-fluoro, 2'-allyl, 2'-O-[2-(methylamino)-2-oxoethyl], 2'-hydroxyl (RNA), 4'-thio, 4'-CH$_2$—O-2'-bridge, 4'-(CH$_2$)$_2$—O-2'-bridge, 2'-LNA, and 2'-O-(N-methylcarbamate)). Without being bound to theory, it is hypothesized that incorporating one or more 2' modified nucleotides in the recognition regions renders those modified regions unsuitable to serve as template for polymerase extension in nonspecific intermolecular and/or intramolecular complexes formed by interactions of primers/templates (e.g., primer-dimer formation), and, thereby, reduces or eliminates the background signal in isothermal amplification. The 2' modified nucleotide preferably has a base that base pairs with the target sequence. In particular embodiments, two or more 2' modified nucleotides (e.g., 2, 3, 4, 5 or more 2' modified nucleotides) in the target specific recognition region are contiguous (e.g., a block of modified nucleotides). In some embodiments, the block of 2' modified nucleotides is positioned at the 3' end of the target specific recognition region. In other embodiments, the block of 2' modified nucleotides is positioned at the 5' end of the target specific recognition region. When the block of 2' modified nucleotides is positioned at the 5' end of the target specific recognition region, the 2' modified nucleotides may be separated from the nick site by one or more non-modified nucleotides (e.g., 2, 3, 4, 5 or more 2' unmodified nucleotides). Applicants have found that positioning of one or more 2' modified nucleotides or of a block of 2' modified nucleotides alters the kinetics of amplification. When the one or more 2' modified nucleotides or block of 2' modified nucleotides are positioned at or near the 5' end of the recognition region or proximal to the nick site, real-time amplification reactions showed decreased time to detection. Additionally, the signal curve was contracted and the slope of the curve shifted. The applicants have also found that in recognition regions exceeding 12 nucleotides in length a single block of 5 consecutive 2'-modified nucleotide is not sufficient to suppress nonspecific amplification and therefore the entire recognition region up to 4 or 5 nucleotides downstream from the nick site must be substituted by 2'-modified nucleotides alternating with unmodified nucleotides.

In a related embodiment, ratios of a primer/template oligo having one or more 2' modified nucleotides can be used to alter the time-to-detection and/or the efficiency of the reaction for the 'tuning' of reactions, resulting in a predictable control over amplification kinetics. Increasing the ratio of primer/template oligo having one or more 2' modified nucleotides at the 3'-end of the recognition sequence to primer/template oligo having one or more 2' modified nucleotides at the 5' end of the recognition sequence contracted the signal curve and shifted the slope of the curve. It is advantageous to be able to "tune" a reaction providing a means to manipulate both the time-to-detection as well as the efficiency of the reaction. Relative quantification using an internal control requires that two important conditions be met. First, it is beneficial to be able to modify a reaction's time-to-detection creating a non-competitive reaction condition. Thus, by affecting the control reaction to be detectable at a later time-point (relative to the target of interest) the control reaction does not out-compete the specific target of interest even when the target of interest is in low initial abundance. Second, to ensure a true relative abundance calculation, it is required that the control and specific target reactions have matched efficiencies. By controlling the efficiency of each reaction using a "tuning" condition enables reactions to be matched allowing for satisfactory relative quantification calculations. Tuning the reactions can be used to match efficiencies of target nucleic acid amplification and reference nucleic acid amplification (e.g., internal standard) in quantitative PCR (qPCR). Additionally, amplification curves of the target nucleic acid and the internal standard may be altered so time of detection of their amplification products are separated, while providing the same efficiency for target nucleic acid amplification and internal standard amplification. Through the use of specific combinations and ratios of oligonucleotide structures within a reaction it is possible to create conditions which enable tuned reaction performance.

In various embodiments, primer/template pairs are constructed with a stem and loop configuration. The 5' end of the primer/template oligonucleotide comprises a self-complementary region that forms at least part of the stem. In some embodiments of the invention the stem further encompasses at least a portion or all of the nicking enzyme recognition sequence. In other various embodiments of the invention the nicking enzyme recognition sequence in the primers-templates is not part of the double stranded stem structure, but resides within the mostly single stranded loop. This nicking enzyme recognition site is linked at the 3' end to a secondary-structure-free site comprising a nicking site that is linked at the 3' end to a sequence that is complementary to a target sequence. If desired, the sequence that is complementary to the target sequence may comprise a secondary structure or may be free of secondary structure. The presence of absence or secondary structure, which may comprise a self-complementary region, will be determined to optimize the particular NEAR assay.

In one embodiment, the methods of the invention provide a NEAR reaction that comprises the standard NEAR components, but also comprises an enzyme capable of nicking a RNA nucleotide when present in a heteroduplex with a complementary DNA strand. In one example, the cleaved RNA nucleotide will be present in a string of 4-15 non-cleavable RNA nucleotides (i.e. O-2-Me-RNAs) toward the 5' end of the target complementary region of the PTO, and the 3' end of the template oligonucleotide will have a 3' terminal 'cap'. Only upon complete proper hybridization of the template oligonucleotide, with the heteroduplex cleaving molecule (i.e. RNase H) will be able to cleave the RNA base, creating a 3' end for the nick translation enzyme to extend from; and allowing the NEAR reaction to progress to completion. Aberrant template binding (primer dimers, partial non-target hybridization, etc) will not lead to the RNA-DNA heteroduplex to form; and thus prevent the progression of the NEAR reaction. These templates will only be amplified after binding to a complementary nucleotide sequence through the removal of the 3' polymerase extension 'cap'. This will lead to an increased level of specificity and sensitivity of the NEAR reaction.

The template oligonucleotides of the invention are included in a NEAR reaction that comprises (1) a target nucleic acid molecule; (2) two template oligonucleotide molecules comprising some number of oligonucleotides that are complementary to the target nucleic acid molecule and a site that can be cleaved by a nicking enzyme and comprised of 4-15 RNA nucleotides, one of which is RNase liable; (3) dNTPs; (4) a strand displacing polymerase; (5) a nicking enzyme; and (6) a DNA-RNA heteroduplex RNA nicking enzyme and a 3' terminal polymerase extension cap. Accordingly, the invention provides a method of using these components to quantitate a target nucleic acid molecule.

The method involves contacting a target nucleic acid molecule under substantially isothermal conditions with a polymerase, two template oligonucleotides, each of which specifically binds to a complementary sequence on the target nucleotide molecule, a nicking enzyme, and a DNA-RNA heteroduplex nicking enzyme (e.g. RNase H) with a 3' terminal polymerase extension cap; generating a detectable amplicon that comprises at least a portion of a template oligonucleotide that binds a target sequence.

Target Nucleic Acid Molecules

Methods and compositions of the invention are useful for the identification of a target nucleic acid molecule in a test sample. The target sequences is amplified from virtually any samples that comprises a target nucleic acid molecule, including but not limited to samples comprising fungi, spores, viruses, or cells (e.g., prokaryotes, eukaryotes). In specific embodiments, compositions and methods of the invention detect *Clavibacter michiganensis* subsp. *michiganensis*, *Clavibacter michiganensis* subsp. *sepedonicus*, *Pseudomonas syringae* pv *Tomato*, *Xanthomonas campestris* pv *Vesicatoria*, *Alternaria* spp, *Cladosporium* spp, *Fusarium oxysporum*, *Verticilium dahlia*, *Pseudomonas currugata*, *Erwina carotovora*, and *Ralstonia solanacearum*. Exemplary test samples include body fluids (e.g. blood, serum, plasma, amniotic fluid, sputum, urine, cerebrospinal fluid, lymph, tear fluid, feces, or gastric fluid), tissue extracts, culture media (e.g., a liquid in which a cell, such as a pathogen cell, has been grown), environmental samples, agricultural products or other foodstuffs, and their extracts, DNA identification tags. If desired, the sample is purified prior to inclusion in a NEAR reaction using any standard method typically used for isolating a nucleic acid molecule from a biological sample.

In one embodiment, primer/template oligonucleotides amplify a target nucleic acid of a pathogen to detect the presence of a pathogen in a sample. Exemplary pathogens include fungi, bacteria, viruses and yeast. Such pathogens may be detected by identifying a nucleic acid molecule encoding a pathogen protein, such as a toxin, in a test sample. Exemplary toxins include, but are not limited to aflatoxin, cholera toxin, diphtheria toxin, Salmonella toxin, Shiga toxin, *Clostridium botulinum* toxin, endotoxin, and mycotoxin. For environmental applications, test samples may include water, liquid extracts of air filters, soil samples, building materials (e.g., drywall, ceiling tiles, wall board, fabrics, wall paper, and floor coverings), environmental swabs, or any other sample.

In one embodiment disclosed herein, primer/template oligonucleotides amplify a target nucleic acid of plant used as an internal control in molecular breeding experiments geared towards improving, for example, the plant's resistance to drought, the plant's resistance to herbicides, to predation by harmful insects. One example of such an internal control target nucleic reduced to praxis herein is the ADH1 gene (alcoholdehydrogenase 1) from corn.

Target nucleic acid molecules include double-stranded and single-stranded nucleic acid molecules (e.g., DNA, RNA, and other nucleobase polymers known in the art capable of hybridizing with a nucleic acid molecule described herein). RNA molecules suitable for detection with a detectable oligonucleotide probe or detectable primer/template oligonucleotide of the invention include, but are not limited to, double-stranded and single-stranded RNA molecules that comprise a target sequence (e.g., messenger RNA, viral RNA, ribosomal RNA, transfer RNA, micro-RNA and microRNA precursors, and siRNAs or other RNAs described herein or known in the art). DNA molecules suitable for detection with a detectable oligonucleotide probe or primer/template oligonucleotide of the invention include, but are not limited to, double stranded DNA (e.g., genomic DNA, plasmid DNA, mitochondrial DNA, viral DNA, and synthetic double stranded DNA). Single-stranded DNA target nucleic acid molecules include, for example, viral DNA, cDNA, and synthetic single-stranded DNA, or other types of DNA known in the art.

In general, a target sequence for detection is between 10 and 100 nucleotides in length (e.g., 10, 15, 20, 25, 30, 35, 40, 45, 50, 60, 70, 80, 90, 100 nucleotides. The GC content of the target nucleic acid molecule is selected to be less than about 45, 50, 55, or 60%. Desirably, the target sequence and nicking enzymes are selected such that the target sequence does not contain nicking sites for any nicking enzymes that will be included in the reaction mix.

Detectable Oligonucleotide Probes

The present invention provides for the quantitative detection of target nucleic acid molecules or amplicons thereof in a NEAR reaction using non-amplifiable detectable polynucleotide probes comprising at least one polymerase-arresting molecule (e.g., nucleotide modification or other moiety that renders the oligonucleotide capable of binding a target nucleic acid molecule, but incapable of supporting template extension utilizing the detectable oligonucleotide probe as a target). Without wishing to be bound by theory, the presence of one or more moieties which does not allow polymerase progression likely causes polymerase arrest in non-nucleic acid backbone additions to the oligonucleotide or through stalling of a replicative polymerase (i.e.

C3-spacer, damaged DNA bases, other spacer moiety, O-2-Me bases). These constructs thus prevent or reduce illegitimate amplification of the probe during the course of a NEAR reaction. This distinguishes them from conventional detection probes, which must be added at the end of the NEAR reaction to prevent their amplification.

Conventional detection probes have proven impractical for quantitating a NEAR reaction in real time. If conventional detection probes are incorporated into the NEAR reaction, these conventional detection probes are amplified concurrently with the target. The amplification of these detection molecules masks the detection of legitimate target amplicons due to the number of starting molecules of the detection probe at the start of the reaction.

The invention provides non-amplifiable detectable polynucleotide probe that comprise least one polymerase-arresting molecule. A polymerase-arresting molecule of the invention includes, but is not limited to, a nucleotide modification or other moiety that blocks primer-template extension by replicative DNA polymerases, thereby preventing the amplification of detection molecules; but can allow proper hybridization or nucleotide spacing to the target molecule or amplified copies of the target molecule. In one embodiment, a detectable oligonucleotide probe of the invention comprises a 3 carbon spacer (C3-spacer) that prevents or reduces the illegitimate amplification of a detection molecule.

In one embodiment, the detectable oligonucleotide probe of the invention is a hair-pin shaped oligonucleotide comprising a detectable moiety. In another embodiment, the non-amplifiable detectable polynucleotide probe is a hair-pin shaped oligonucleotide that comprises a fluorophore on one end and a quenching dye on the opposite end. The loop of the hair-pin comprises a sequence that is complementary to and capable of hybridizing with a target sequence. The stem of the hair-pin is formed by annealing of complementary arm sequences located on either side of the loop. A fluorophore and a quenching molecule are covalently linked at opposite ends of each arm. When the detectable oligonucleotide probe is in the hair pin configuration, the fluorescent and quenching molecules are proximal to one another, thereby leading to fluorescence resonance energy transfer (FRET) and quenching of the fluorescence of the fluorophore. When the detectable oligonucleotide probe encounters a target molecule, hybridization occurs; the loop structure is converted to a duplex conformation with the target molecule, causing separation of the fluorophore and quencher molecules resulting in fluorescence (Tyagi et al. Nature Biotechnology 14: March 1996, 303-308).

The detectable oligonucleotide probes are specific to the target sequence. In one embodiment, a detectable oligonucleotide probe comprises one or more modified nucleotide bases having enhanced binding affinity to a complementary nucleotide. Examples of bases include, but are not limited to locked nucleic acids (LNA), 2' Fluoro amidites, and 2'OMe RNA amidites (also functioning as a polymerase arresting molecule). Detectable oligonucleotide probes of the invention can be synthesized with different colored fluorophores and may be designed to hybridize with virtually any target sequence. In view of their remarkable specificity, a non-amplifiable detectable polynucleotide probe of the invention is used to detect a single target nucleic acid molecule in a sample, or is used in combination with detectable oligonucleotide probes each of which binds a different target nucleic acid molecule. Accordingly, the non-amplifiable detectable polynucleotide probes of the invention may be used to detect one or more target nucleic acid molecules in the same reaction, allowing these targets to be quantitated simultaneously. The present invention encompasses the use of such fluorophores in conjunction with the detectable oligonucleotide probes described herein.

Use of Non-Amplifiable Detectable Polynucleotide Probes

Non-amplifiable detectable polynucleotide probe are useful in methods for quantitating a target nucleic acid molecule in a nicking and extension amplification reaction (NEAR). The method involves contacting a target nucleic acid molecule under substantially isothermal conditions with a polymerase, two primer/template oligonucleotides, each of which specifically binds to a complementary sequence on the target nucleotide molecule, a nicking enzyme, and the detectable oligonucleotide probe in the presence of a suitable buffer and dNTPs, generating amplicons comprising at least a portion of said target nucleic acid molecule; and determining the level of target nucleic acid molecule present in the reaction by quantitating the oligonucleotide probe that hybridizes to the target nucleic acid molecule in real time during the reaction based on fluorescent intensity from the probe molecules in the reaction. Advantageously, such methods are useful for monitoring NEAR in real time.

In general, non-amplifiable detectable polynucleotide probes of the invention are included in a NEAR reaction that comprises (1) a target nucleic acid molecule; (2) two template oligonucleotide molecules comprising some number of oligonucleotides that are complementary to the target nucleic acid molecule and a site that can be cleaved by a nicking enzyme; (3) dNTPs; (4) a strand displacing polymerase; and (5) a nicking enzyme. Accordingly, the invention provides a method of using these components to quantitate a target nucleic acid molecule.

NEAR Assays

The invention provides for the detection of target nucleic acid molecules amplified in a NEAR assay. Such assays are known in the art and described herein. See, for example, US Patent Application Publication 2009/0081670, PCT Application 2009/012246, and U.S. Pat. Nos. 7,112,423 and 7,282,328, each of which is incorporated herein in its entirety. Polymerases useful in the methods described herein are capable of catalyzing the incorporation of nucleotides to extend a 3' hydroxyl terminus of an oligonucleotide (e.g., a primer/template oligonucleotide or other primer) bound to a target nucleic acid molecule. Such polymerases include those that are thermophilic and/or those capable of strand displacement. Polymerases useful in methods described herein lack a 5'-3' exonuclease activity, which would otherwise degrade the displaced single stranded nucleic acid strand. olymerase also has reverse transcriptase activity (e.g., derivatives of Bst (large fragment) DNA polymerase, Terminator DNA polymerase, Terminator II DNA polymerase). Exemplary polymerases include, but are not limited to the Bst large fragments of Bst DNA polymerase I, E. coli DNA polymerase I (Klenow fragment), Klenow fragment (3'-5' exo-), T4 DNA polymerase, T7 DNA polymerase, Deep VentR. (exo-) DNA Polymerase, Deep VentR DNA Polymerase, Terminator, Terminator II DNA Polymerase, AmpliTherm DNA Polymerase, SP6 DNA polymerase. The following non-limiting examples of Reverse Transcriptases (RT) can be used in the reactions of the present method to improve performance when detecting an RNA sequence: OmniScript (Qiagen), SensiScript (Qiagen), MonsterScript (Epicentre), Transcriptor (Roche), HIV RT (Ambion), SuperScript III (Invitrogen), ThermoScript (Invitrogen), Thermo-X (Invitrogen), ImProm II (Promega).

A nicking enzyme binds to a recognition sequence in double-stranded DNA and cleaves one strand of a double-stranded helix. Nicking enzymes may cleave either upstream or downstream of their recognition site or within the enzyme's recognition site. For methods disclosed herein, only nicking enzymes that cleave the top strand downstream of the recognition site can be used to launch repetitive cycles of substrate DNA nicking and nick extension by the polymerase to drive exponential amplification of the target nucleic fragment between the primer-templates. Ideally, the nicking enzyme is functional under the same reaction conditions as the polymerase. In a preferred embodiment of the invention, the nicking enzyme is thermostable and active between 50° C. and 60° C. Exemplary nicking enzymes useful for methods disclosed herein include, but are not limited to, Nt.BspQI(NEB), Nt.BspD6I, Nt.BsmAI(NEB), Nt.AlwI(NEB), Nt.BbvCI(NEB), N.Bst9I(Sibenzyme), and Nt.BstNBI(NEB).

A NEAR reaction typically comprises nucleotides, such as, for example, dideoxyribonucleoside triphosphates (dNTPs). The reaction may also be carried out in the presence of dNTPs that comprise a detectable moiety including but not limited to a radiolabel (e.g., $^{32}P$, $^{33}P$, $^{125}I$, $^{35}S$) an enzyme (e.g., alkaline phosphatase), a fluorescent label (e.g., fluorescein isothiocyanate (FITC)), biotin, avidin, digoxigenin, antigens, haptens, or fluorochromes. The NEAR reaction further comprises certain salts and buffers that provide for the activity of the nicking enzyme and polymerase.

Advantageously, the NEAR reaction is carried out under substantially isothermal conditions where the temperature of the reaction is more or less constant during the course of the amplification reaction. Because the temperature does not need to be cycled between an upper temperature and a lower temperature, the NEAR reaction can be carried out under conditions where it would be difficult to carry out conventional PCR. Typically, the reaction is carried out at about between 35° C. and 90° C. (e.g., 35, 37, 42, 60, 65, 70, 75, 80, or 85° C.). Advantageously, it is not essential that the temperature be maintained with a great degree of precision. Some variability in temperature is acceptable.

Melt temperature (Tm) and reaction rate modifiers may also be used to lower the melting temperature of the oligonucleotides, such as (but not limited to) ethylene glycol and glycerol. In addition, DNA polymerase reaction rate modifiers (such as dNTP and magnesium concentration) may be used to alter the reaction rate to lead to a greater quantification precision.

This invention provides methods of monitoring a NEAR reaction in real time, utilizing NEAR amplification strategy as described above and in U.S. Pat. No. 7,112,423B2 and US20090017452A1. In one embodiment, quantitative NEAR utilizes target nucleic acids amplification alongside a control amplification of known quantity. The amount of target nucleic acid can be calculated as an absolute quantification or a relative quantification (semi-quantitative) based on the source of the control (exogenous or endogenous control).

Quantitation of the unknown nucleotide sequence can be achieved either through comparison of logarithmic threshold amplification of the unknown to a series of known target sequences in either a separate set of reactions or in the same reaction; or as an internal endogenous or exogenous co-amplification product which produces a threshold value, indicative of either a positive result (if the unknown exceeds the threshold) or negative result (if the unknown does not exceed the threshold).

Applications

The present invention provides for the real-time monitoring of the isothermal amplification NEAR reaction which can provide a quantitative measure of the amount of the starting target nucleic acid. Compositions and methods of the invention are useful in human diagnostics, where a rapid quantitative answer is desired (e.g., detectable amplification in under 15, 10, 9, 8, 7, 6, 5 min. or less). In particular embodiments, the invention provides for the use of NEAR reaction assays in human diagnostics in clinical settings. In other embodiments, the invention provides for the use of NEAR reaction assays in diagnostic field work, where access to thermocycling equipment is unavailable or would be prohibitively expensive. In still other embodiments, the invention provides for the use of NEAR reaction assays in an academic setting where rapid quantitative answers are desired.

Kits

The invention also provides kits for the amplification of a target nucleic acid molecule. Such kits are useful for the detection or quantitation of a target nucleic acid in a biological sample obtained from a subject. Kits of the present invention may comprise, for example, one or more polymerases, forward and reverse primer-templates, and one or more nicking enzymes, as described herein. Where one target is to be amplified, one or two nicking enzymes may be included in the kit. Where multiple target sequences are to be amplified, and the primer-templates designed for those target sequences comprise the nicking enzyme sites for the same nicking enzyme, then one or two nicking enzymes may be included. Where the primer-templates are recognized by different nicking enzymes, more nicking enzymes may be included in the kit, such as, for example, 3 or more.

In one aspect, the invention provides a kit for nucleic acid amplification comprising a DNA polymerase; a primary primer-template, a secondary primer-template, a nicking enzyme with specificity to a nicking enzyme recognition site within the primer-templates, and deoxynucleotide triphosphates (dNTP's) (e.g., in a buffered solution containing components sufficient for amplification). In various embodiments, the primary primer-template and secondary primer-template, each have a 3'-end specific recognition region sequence complementary or substantially complementary to the target sequence, where the end specific recognition region comprises one or more 2' modified nucleotides; a 5'-end tail sequence containing a nicking enzyme recognition site upstream of the 3'-end specific recognition region sequences; and a stabilizing sequence upstream (5') of the nicking enzyme binding site.

In one aspect, the kits of the present invention comprise a homogenous mix of all NEAR reaction components, including, but not limited to, dNTP's, forward and reverse primer-templates, nicking enzyme, polymerase, a detectable target specific polynucleotide probe, reaction buffer and stabilizers, except the target nucleic acid.

The kits of the present invention may also comprise one or more of the components in any number of separate containers, packets, tubes (e.g., <0.2 ml, 0.2 ml, 0.6 ml, 1.5 ml, 5.0 ml, >5.0 ml), vials, microtiter plates (e.g., <96-well, 96-well, 384-well, 1536-well, >1536-well), ArrayTape, and the like, or the components may be combined in various combinations in such containers. In various embodiments, the kit further comprises a pair of primer-template oligonucleotides capable of binding to and amplifying a reference sequence. In yet other embodiments, the kit comprises a sterile container which contains the primer-template oligonucleotides; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids.

The components of the kit may, for example, be present in one or more containers, for example, all of the components may be in one container, or, for example, the enzymes may be in a separate container from the templates. The components may, for example, be dried (e.g., dry residue), lyophilized (e.g., dry cake) or in a stable buffer (e.g., chemically stabilized, thermally stabilized). Dry components may, for example, be prepared by lyophilization, vacuum and centrifugal assisted drying and/or ambient drying. In various embodiments, the polymerase and nicking enzymes are in lyophilized form in a single container, and the templates are either lyophilized, freeze dried, or in buffer, in a different container. In some embodiments, the polymerase, nicking enzymes, and the templates are, in lyophilized form, in a single container. In other embodiments, the polymerase and the nicking enzyme may be separated into different containers.

Kits may further comprise, for example, dNTPs used in the reaction, or modified nucleotides, cuvettes or other containers used for the reaction, or a vial of water or buffer for re-hydrating lyophilized components. The buffer used may, for example, be appropriate for both polymerase and nicking enzyme activity.

The kits of the present invention may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

Kits may further comprise reagents used for detection methods (e.g., real-time or endpoint), such as, for example, hybridization probes or DNA binding dyes. Kits may further comprise reagents used for detection methods, such as, for example, reagents used for FRET, lateral flow devices, dipsticks, fluorescent dye, colloidal gold particles, latex particles, a molecular beacon, or polystyrene beads. Detection components may be incorporated into a lateral flow device. The lateral flow device may be used at a point of care.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Currently, the NEAR reaction is used to quickly and isothermally detect the presence or absence of a target oligonucleotide in a sample. Due to technical limitations, conventional NEAR methods are unsuitable for quantifying target oligonucleotides in real time due, at least in part, to illegitimate amplification of non-target molecules in the sample, which obscures the detection and accurate quantification of target amplicons. The present invention provides compositions and methods that overcome these limitations by providing detectable primer/templates that are not susceptible to illegitimate amplification. In one embodiment, a quantifiable NEAR assay employs a primer comprising one or more 2'-O-Me modifications that prevents or reduces the illegitimate amplification of non-target molecules during the NEAR reaction. Currently, the design of NEAR amplification assays is limited to very short regions within the target nucleic acid that have at least one naturally occurring nicking enzyme recognition site in close proximity. Strand displacement synthesis initiated from this nick site provides single stranded target DNA molecules to which primer-templates with short target specific regions can bind and start the cycles of nicking/polymerase extension target amplification reactions. The present invention provides compositions and methods that overcome this limitation by utilizing primer-templates with longer target specific regions, which therefore are capable of strand invasion between 50° C. to 60° C. during the first phase of the amplification reaction without the assistance of strand displacement synthesis. Longer target specific regions in primer-templates come with the disadvantage of providing more real estate to form nonspecific DNA hybrids with extendable 3'-ends that can launch synthesis of nonspecific amplification products. Compositions in the present invention mitigate that disadvantage by extending the placement of 2'-modified nucleotides beyond a 3'-terminal block of five consecutive modified nucleotides to cover the entire target specific region utilizing an alternate sequence of 2'-modified and unmodified nucleotides.

Example 1: Primer-Template Oligonucleotides Comprising 2'-O-Methyl Nucleotides Reduce or Eliminate Background Signal in NEAR Amplification When NEAR amplification is performed without input target nucleic acid (i.e., No Target Controls; NTC's) signal is generated despite the absence of template. Thus, generation of background signal has the potential to decrease the accuracy of target nucleic acid quantitation using NEAR amplification. It was hypothesized that the background signal was generated, in part, by formation of primer-dimers by primer/template oligonucleotides. Without being bound to theory, polymerase arresting structures comprising 2' modified nucleotides could by used to reduce or eliminate intermolecular and/or intramolecular interactions of primers/templates (e.g., primer-dimer formation), and, thereby, reduce or eliminate the background signal in NEAR assay.

Exemplary polymerase-arresting entity structures from 5' to 3' comprise a stabilizer sequence, nicking enzyme recognition sequence, nicking enzyme spacer sequence, and target specific recognition sequence, the target specific recognition sequence comprising one or more 2' modified nucleotides (e.g., 2'-O-methyl ribonucleotides). Where two or more 2' modified nucleotides are present in the target specific recognition sequence the 2' modified nucleotides may be contiguous (e.g., 2, 3, 4, 5 or more 2' modified nucleotides). Titration of *Clavibacter michiganensis sepidonicus* (Cms) synthetic double stranded target DNA molecule was evaluated using detection via a fluorobeacon. Target DNA was serially diluted from a stock solution of a synthesized 250 basepair DNA 'longmer' which was designed with the target sequence and a single nick site.

The signal in the No Target Controls (NTC's) was suppressed in the 2'-O-methyl modified template-containing reactions (FIG. 2A). The Standard Curve displayed a wide dynamic range using the 2'-O-methyl template reactions (FIG. 2B). Samples (10 μl) of the No Target Control reactions were analyzed via HPLC/Mass Spectrometry and confirmed suppression of background amplification products (FIG. 2C). The spectra derived from reactions using unmodified oligos showed a complex spectrum composed of multiple amplification products derived from non-specific background products along with unreacted templates (FIG. 2C, left panel). The spectra derived from reactions using 2'-O-methyl modified oligos showed a simple spectrum composed of unreacted templates without the presence of non-specific background products (FIG. 2C, right panel).

To study the effect of the 2'-O-methyl modified template-containing reactions on the amplification of a biological sample, genomic *Clavibacter michiganensis sepidonicus* (Cms) was used as target DNA. Amplified products were detection by SYBR green, which detects double-stranded DNA (FIGS. 3A and 3B) or Molecular Beacons, which detected a specific product (FIGS. 4A and 4B). Standard reactions were carried out with DNA oligonucleotide templates (FIGS. 3A and 4A) and 2'-O-methyl modified template-containing reactions (DNAble) reactions were carried out with oligonucleotides containing a block of 5 contiguous 2'-O-methyl nucleotides at the 3'-end in the target specific recognition sequence (FIGS. 3B and 4B). The signal in the No Target Controls (NTC's) was suppressed in the 2'-O-methyl modified template-containing reactions (FIGS. 3B and 4B) whereas significant signal is observed in the No Target Controls (NTC's) (FIGS. 4A and 4B) indicating generation of background product in the absence of target DNA.

Thus, these results indicate that primers comprising 2'-O-methyl nucleotides reduce or eliminate background signal in NEAR amplification.

Example 2: Positioning of 2'-O-Methyl Nucleotides in Primer/Template Oligonucleotides Altered Time-to-Detection and Efficiency of NEAR Reactions Exemplary polymerase arresting entities having 2'-O-methyl modified nucleotides at different positions within the specificity region were used in NEAR amplification reactions and their reaction kinetics studied. In particular, the primer/templates studied included a pair of oligonucleotides having a block of five 2'-O-methyl nucleotides placed at the 3' end of the specificity region or at the 5' end of the specificity region (2 nucleotides downstream of the nick site) (FIG. 5). Standard reactions were carried out in duplicate with a block of 2'-O-methyl nucleotides on the 3'-end or starting at the $3^{rd}$ nucleotide after the nick site and continuing for 5 bases or a mixture of these two structures as indicated. Target DNA was genomic *Clavibacter michiganensis sepidonicus* (Cms). Detection was based on Molecular Beacon at a final concentration of 100 nM.

Reaction rate modifying entities having 2'-O-methyl modified nucleotides at different positions within the specificity region of the primer/template oligonucleotide displayed different amplification kinetics (FIG. 6). The reactions using primer/templates having a block of five 2'-O-methyl nucleotides at the 3' end showed decreased time to detection ("Terminal" template; 170 sec) compared to primer/templates having a block of five 2'-O-methyl nucleotides starting at the $3^{rd}$ nucleotide after the nick site ("Nick+2" template"; 430 sec). Thus, it was hypothesized that ratios of the two primer/template oligos can be used to manipulate the time-to-detection and/or the efficiency of the reaction for the 'tuning' of reactions. Reactions with varying ratios of "Terminal" template:"Nick+2" template showed intermediate time-to-detection between that of the two templates (FIG. 6). Additionally, with increasing ratio of "Terminal" template:"Nick+2" template, the curve was contracted and the slope of the curve shifted. Thus, it was shown that positioning of 2' modified nucleotides in primer/template oligonucleotides and ratios of primer/template oligonucleotides with differentially positioned 2' modified nucleotides altered time-to-detection and efficiency of NEAR reactions. The invention is at least based in part on these discoveries.

Example 3: Complete Suppression of Nonspecific Amplification in NEAR Assays Utilizing Primer-Templates with Long Target Specific Regions A NEAR assay for the quantification of the corn alcohol dehydrogenase 1 gene (ADH1) was designed utilizing two alternative sets of forward and reverse primer-templates (TS3 & TS3). No suitable nicking enzyme recognition site could be located within 500 nucleotides upstream or downstream from the target sequence region in corn gDNA. Both sets of primers-templates feature longer target complementary regions (16 and 19 nucleotides, respectively) capable of strand invasion mediated hybridization with the target DNA. In the first set (TS3) the target complementary regions of the forward and reverse primer-templates contain a block of 5 consecutive 2'-O-methyl modified ribonucleotides immediately upstream from the 3'-terminal deoxynucleotide. The remainder of the target sequence complementary region comprises a sequence of alternating unmodified deoxynucleotides and 2'-O-methyl ribonucleotides starting five nucleotides (forward primer-template) or four nucleotides (reverse primer-template) downstream from the nick site. The second set (TS6) of primer-templates features only a block of five 2'-O-methyl ribonucleotides adjacent to the 3'-terminal unmodified deoxynucleotide, while the rest of the target complementary region comprises only unmodified dexynucleotides.

Ten microliter NEAR reactions were set up in 50 mM Tris pH 8.0, 15 mM $(NH_4)_2SO_4$, 15 mM $Na_2SO_4$, and 15 mM $MgSO_4$ using 3.84 U Warmstart 2.0 Bst DNA polymerase 1 (NEB), 10K copies of synthetic corn ADH1 target DNA, 0.3 mM dNTP's, 3 U Nt.BstNBI nicking enzyme, 200 nM ROX/BHQ-labeled ADH1 molecular beacon probe, 0.5× SYBRgreen dye (LifeTechnologies), 1000 nM TS3 or TS6 reverse primer-template and 100 nM TS3 or TS6 forward primer-template. A set of no target DNA control reactions (NTC) were made up of the same components without the synthetic corn ADH1 target DNA. All reactions were incubated at 56° C. for 15 minutes and fluorescence signals recorded at 520 nm (SYBRgreen) and 610 nm (ROX).

Comparing the amplification plots of the target DNA containing reactions in the SYBRgreen (FIG. 8A) and ROX (FIG. 8B) detection channels with amplification plots of the NTC reactions in the SYBRgreen detection channel (FIG. 8C)

Results reported herein were obtained using the following methods and materials unless indicated otherwise.

NEAR Amplification Reactions

Reactions (50 µl) contained 15 mM $MgSO_4$, 0.3 mM dNTPs, 19.2 units Bst Polymerase, 15 units n.BstNBI, 1000 nM template 1, and 200 nM template 2. Target DNA was genomic *Clavibacter michiganensis sepidonicus* (Cms) or a "longmer" based on Cms s <213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (24)..(24)
<223> OTHER INFORMATION: 2'-O-methyl modified RNA base

<400> SEQUENCE: 3
tgactccata tggagtcaca tggutcattc gtg                                    33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(25)
<223> OTHER INFORMATION: 2'-O-methyl modified RNA base

<400> SEQUENCE: 4
tgactccata tggagtcaca tggtucattc gtg                                    33

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (26)..(26)
<223> OTHER INFORMATION: 2'-O-methyl modified RNA base

<400> SEQUENCE: 5
tgactccata tggagtcaca tggttcattc gtg                                    33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (27)..(27)
<223> OTHER INFORMATION: 2'-O-methyl modified RNA base

<400> SEQUENCE: 6
tgactccata tggagtcaca tggttcattc gtg                                    33

<210> SEQ ID NO 7
<211> LENGTH: 33

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (28)..(28)
<223> OTHER INFORMATION: 2'-O-methyl modified RNA base

<400> SEQUENCE: 7
tgactccata tggagtcaca tggttcautc gtg                                    33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (29)..(29)
<223> OTHER INFORMATION: 2'-O-methyl modified RNA base

<400> SEQUENCE: 8
tgactccata tggagtcaca tggttcatuc gtg                                    33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(30)
<223> OTHER INFORMATION: 2'-O-methyl modified RNA base

<400> SEQUENCE: 9
tgactccata tggagtcaca tggttcattc gtg                                    33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (31)..(31)
<223> OTHER INFORMATION: 2'-O-methyl modified RNA base

<400> SEQUENCE: 10
tgactccata tggagtcaca tggttcattc gtg                                    33

<210> SEQ ID NO 11
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (32)..(32)
<223> OTHER INFORMATION: 2'-O-methyl modified RNA base

<400> SEQUENCE: 11
tgactccata tggagtcaca tggttcattc gug                                33

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (33)..(33)
<223> OTHER INFORMATION: 2'-O-methyl modified RNA base

<400> SEQUENCE: 12
tgactccata tggagtcaca tggttcattc gtg                                33

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(23)
<223> OTHER INFORMATION: 2'-O-methyl modified RNA base

<400> SEQUENCE: 13
tgactccata tggagtcaca tggttcattc gtg                                33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(24)
<223> OTHER INFORMATION: 2'-O-methyl modified RNA base

<400> SEQUENCE: 14
tgactccata tggagtcaca tggutcattc gtg                                33
```

```
<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (24)..(25)
<223> OTHER INFORMATION: 2'-O-methyl modified RNA base

<400> SEQUENCE: 15
tgactccata tggagtcaca tgguucattc gtg                                33

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(26)
<223> OTHER INFORMATION: 2'-O-methyl modified RNA base

<400> SEQUENCE: 16
tgactccata tggagtcaca tggtucattc gtg                                33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (26)..(27)
<223> OTHER INFORMATION: 2'-O-methyl modified RNA base

<400> SEQUENCE: 17
tgactccata tggagtcaca tggttcattc gtg                                33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (27)..(28)
<223> OTHER INFORMATION: 2'-O-methyl modified RNA base

<400> SEQUENCE: 18
tgactccata tggagtcaca tggttcautc gtg                                33
```

```
<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (28)..(29)
<223> OTHER INFORMATION: 2'-O-methyl modified RNA base

<400> SEQUENCE: 19
tgactccata tggagtcaca tggttcauuc gtg                                   33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (29)..(30)
<223> OTHER INFORMATION: 2'-O-methyl modified RNA base

<400> SEQUENCE: 20
tgactccata tggagtcaca tggttcatuc gtg                                   33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(31)
<223> OTHER INFORMATION: 2'-O-methyl modified RNA base

<400> SEQUENCE: 21
tgactccata tggagtcaca tggttcattc gtg                                   33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (31)..(32)
<223> OTHER INFORMATION: 2'-O-methyl modified RNA base

<400> SEQUENCE: 22
tgactccata tggagtcaca tggttcattc gug                                   33
```

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (32)..(33)
<223> OTHER INFORMATION: 2'-O-methyl modified RNA base

<400> SEQUENCE: 23
tgactccata tggagtcaca tggttcattc gug                                   33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(24)
<223> OTHER INFORMATION: 2'-O-methyl modified RNA base

<400> SEQUENCE: 24
tgactccata tggagtcaca tggutcattc gtg                                   33

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(25)
<223> OTHER INFORMATION: 2'-O-methyl modified RNA base

<400> SEQUENCE: 25
tgactccata tggagtcaca tgguucattc gtg                                   33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (24)..(26)
<223> OTHER INFORMATION: 2'-O-methyl modified RNA base

<400> SEQUENCE: 26

```
tgactccata tggagtcaca tgguucattc gtg                                    33
```

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<221> NAME/KEY: modified_base
<222> LOCATION: (25)..(27)
<223> OTHER INFORMATION: 2'-O-methyl modified RNA base

<400> SEQUENCE: 27

```
tgactccata tggagtcaca tggtucattc gtg                                    33
```

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<221> NAME/KEY: modified_base
<222> LOCATION: (26)..(28)
<223> OTHER INFORMATION: 2'-O-methyl modified RNA base

<400> SEQUENCE: 28

```
tgactccata tggagtcaca tggttcautc gtg                                    33
```

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<221> NAME/KEY: modified_base
<222> LOCATION: (27)..(29)
<223> OTHER INFORMATION: 2'-O-methyl modified RNA base

<400> SEQUENCE: 29

```
tgactccata tggagtcaca tggttcauuc gtg                                    33
```

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<221> NAME/KEY: modified_base
<222> LOCATION: (28)..(30)
<223> OTHER INFORMATION: 2'-O-methyl modified RNA base

<400> SEQUENCE: 30
tgactccata tggagtcaca tggttcauuc gtg                                         33

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (29)..(31)
<223> OTHER INFORMATION: 2'-O-methyl modified RNA base

<400> SEQUENCE: 31
tgactccata tggagtcaca tggttcatuc gtg                                         33

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(32)
<223> OTHER INFORMATION: 2'-O-methyl modified RNA base

<400> SEQUENCE: 32
tgactccata tggagtcaca tggttcattc gug                                         33

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (31)..(33)
<223> OTHER INFORMATION: 2'-O-methyl modified RNA base

<400> SEQUENCE: 33
tgactccata tggagtcaca tggttcattc gug                                         33

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(25)
<223> OTHER INFORMATION: 2'-O-methyl modified RNA base

<400> SEQUENCE: 34
tgactccata tggagtcaca tgguucattc gtg                       33

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(26)
<223> OTHER INFORMATION: 2'-O-methyl modified RNA base

<400> SEQUENCE: 35
tgactccata tggagtcaca tgguucattc gtg                       33

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (24)..(27)
<223> OTHER INFORMATION: 2'-O-methyl modified RNA base

<400> SEQUENCE: 36
tgactccata tggagtcaca tgguucattc gtg                       33

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(28)
<223> OTHER INFORMATION: 2'-O-methyl modified RNA base

<400> SEQUENCE: 37
tgactccata tggagtcaca tggtucautc gtg                       33

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (26)..(29)
<223> OTHER INFORMATION: 2'-O-methyl modified RNA base

```
<400> SEQUENCE: 38
tgactccata tggagtcaca tggttcauuc gtg                                  33

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (27)..(30)
<223> OTHER INFORMATION: 2'-O-methyl modified RNA base

<400> SEQUENCE: 39
tgactccata tggagtcaca tggttcauuc gtg                                  33

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (28)..(31)
<223> OTHER INFORMATION: 2'-O-methyl modified RNA base

<400> SEQUENCE: 40
tgactccata tggagtcaca tggttcauuc gtg                                  33

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (29)..(32)
<223> OTHER INFORMATION: 2'-O-methyl modified RNA base

<400> SEQUENCE: 41
tgactccata tggagtcaca tggttcatuc gug                                  33

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(33)
```

<223> OTHER INFORMATION: 2'-O-methyl modified RNA base

<400> SEQUENCE: 42
tgactccata tggagtcaca tggttcattc gug                        33

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(26)
<223> OTHER INFORMATION: 2'-O-methyl modified RNA base

<400> SEQUENCE: 43
tgactccata tggagtcaca tgguucattc gtg                        33

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(27)
<223> OTHER INFORMATION: 2'-O-methyl modified RNA base

<400> SEQUENCE: 44
tgactccata tggagtcaca tgguucattc gtg                        33

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (24)..(28)
<223> OTHER INFORMATION: 2'-O-methyl modified RNA base

<400> SEQUENCE: 45
tgactccata tggagtcaca tgguucautc gtg                        33

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(29)
<223> OTHER INFORMATION: 2'-O-methyl modified RNA base

<400> SEQUENCE: 46
tgactccata tggagtcaca tggtucauuc gtg        33

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (26)..(30)
<223> OTHER INFORMATION: 2'-O-methyl modified RNA base

<400> SEQUENCE: 47
tgactccata tggagtcaca tggttcauuc gtg        33

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (27)..(31)
<223> OTHER INFORMATION: 2'-O-methyl modified RNA base

<400> SEQUENCE: 48
tgactccata tggagtcaca tggttcauuc gtg        33

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (28)..(32)
<223> OTHER INFORMATION: 2'-O-methyl modified RNA base

<400> SEQUENCE: 49
tgactccata tggagtcaca tggttcauuc gug        33

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:

```
<221> NAME/KEY: modified_base
<222> LOCATION: (29)..(33)
<223> OTHER INFORMATION: 2'-O-methyl modified RNA base

<400> SEQUENCE: 50
tgactccata tggagtcaca tggttcatuc gug                                    33

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(33)
<223> OTHER INFORMATION: 2'-O-methyl modified RNA base

<400> SEQUENCE: 51
tgactccata tggagtcaca tgguucauuc gug                                    33

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(33)
<223> OTHER INFORMATION: 2'-O-methyl modified RNA base

<400> SEQUENCE: 52
tgactccata tggagtcaca tgguucauuc gug                                    33

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (24)..(33)
<223> OTHER INFORMATION: 2'-O-methyl modified RNA base

<400> SEQUENCE: 53
tgactccata tggagtcaca tgguucauuc gug                                    33

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<220> FEATURE:
<221> NAME/KEY: modified_base
<222> LOCATION: (25)..(33)
<223> OTHER INFORMATION: 2'-O-methyl modified RNA base

<400> SEQUENCE: 54
tgactccata tggagtcaca tggtucauuc gug                                  33

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (26)..(33)
<223> OTHER INFORMATION: 2'-O-methyl modified RNA base

<400> SEQUENCE: 55
tgactccata tggagtcaca tggttcauuc gug                                  33

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (27)..(33)
<223> OTHER INFORMATION: 2'-O-methyl modified RNA base

<400> SEQUENCE: 56
tgactccata tggagtcaca tggttcauuc gug                                  33

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (28)..(33)
<223> OTHER INFORMATION: 2'-O-methyl modified RNA base

<400> SEQUENCE: 57
tgactccata tggagtcaca tggttcauuc gug                                  33

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
```

-continued

```
      Synthetic primer
<220> FEATURE:
<221> NAME/KEY: modified_base
<222> LOCATION: (18)..(18)
<223> OTHER INFORMATION: 2'-O-methyl modified RNA base
<220> FEATURE:
<221> NAME/KEY: modified_base
<222> LOCATION: (20)..(20)
<223> OTHER INFORMATION: 2'-O-methyl modified RNA base
<220> FEATURE:
<221> NAME/KEY: modified_base
<222> LOCATION: (22)..(22)
<223> OTHER INFORMATION: 2'-O-methyl modified RNA base
<220> FEATURE:
<221> NAME/KEY: modified_base
<222> LOCATION: (24)..(28)
<223> OTHER INFORMATION: 2'-O-methyl modified RNA base

<400> SEQUENCE: 58
cgcggagtcc tcgaactata agccacgca                                          29

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (19)..(19)
<223> OTHER INFORMATION: 2'-O-methyl modified RNA base
<220> FEATURE:
<221> NAME/KEY: modified_base
<222> LOCATION: (21)..(21)
<223> OTHER INFORMATION: 2'-O-methyl modified RNA base
<220> FEATURE:
<221> NAME/KEY: modified_base
<222> LOCATION: (23)..(23)
<223> OTHER INFORMATION: 2'-O-methyl modified RNA base
<220> FEATURE:
<221> NAME/KEY: modified_base
<222> LOCATION: (25)..(25)
<223> OTHER INFORMATION: 2'-O-methyl modified RNA base
<220> FEATURE:
<221> NAME/KEY: modified_base
<222> LOCATION: (27)..(31)
<223> OTHER INFORMATION: 2'-O-methyl modified RNA base

<400> SEQUENCE: 59
cgcggagtcc gcgtgtacag ctccaccaca ut                                      32

<210> SEQ ID NO 60
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (24)..(29)
<223> OTHER INFORMATION: 2'-O-methyl modified RNA base

<400> SEQUENCE: 60
cgcggagtcc tcgaactata agccacgca                                          29
```

```
<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (27)..(32)
<223> OTHER INFORMATION: 2'-O-methyl modified RNA base

<400> SEQUENCE: 61
cgcggagtcc gcgtgtacag ctccaccaca uu                                     32
```

What is claimed is:

1. An isolated oligonucleotide comprising from 5' to 3',
   i) a first region, and
   ii) a second region,
   wherein the first region comprises a nicking enzyme recognition sequence; wherein the second region comprises at least 9 nucleotides that specifically bind a complementary sequence on a target nucleic acid molecule; and wherein the second region comprises one or more 2' modified nucleotides positioned at the 3' terminus of the sequence complementary to the target nucleic acid molecule.

2. The isolated oligonucleotide of claim 1, wherein the 2' modification is selected from the group consisting of 2'-O-methyl, 2'-methoxyethoxy, 2'-fluoro, 2'-hydroxyl, 2'-allyl, 2'-O-[2-(methylamino)-2-oxoethyl], 4'-thio, 4'-CH$_2$—O-2'-bridge, 4'-(CH$_2$) 2-O-2'-bridge, 2'-LNA, and 2'-O-(N-methylcarbamate) and base analogs.

3. The isolated oligonucleotide of claim 1, wherein two or more 2' modified nucleotides are contiguous.

4. The isolated oligonucleotide of claim 3, wherein the number of contiguous 2' modified nucleotides is 2, 3, 4, 5, or more.

5. The isolated oligonucleotide of claim 4, wherein 5 contiguous 2'-O-methyl modified nucleotides are positioned at the 3' end of the sequence complementary to the target nucleic acid molecule.

6. The isolated oligonucleotide of claim 1, wherein the nicking enzyme recognition sequence is 5'-GAGT-3'.

7. An isolated oligonucleotide comprising from 5' to 3',
   i) a first region, and
   ii) a second region,
   wherein the first region comprises a nicking enzyme recognition sequence; wherein the second region comprises at least 9 nucleotides that specifically bind a complementary sequence on a target nucleic acid molecule; and wherein the second region comprises one or more 2' modified nucleotides positioned at the 5' terminus of the sequence complementary to the target nucleic acid molecule.

8. The isolated oligonucleotide of claim 7, wherein the 2' modification is selected from the group consisting of 2'-O-methyl, 2'-methoxyethoxy, 2'-fluoro, 2'-hydroxyl, 2'-allyl, 2'-O-[2-(methylamino)-2-oxoethyl], 4'-thio, 4'-CH$_2$—O-2'-bridge, 4'-(CH$_2$)$_2$-0-2'-bridge, 2'-LNA, and 2'-O-(N-methylcarbamate) and base analogs.

9. The isolated oligonucleotide of claim 7, wherein the one or more 2' modified nucleotides positioned at the 5' end of the sequence complementary to the target nucleic acid molecule are separated from the nick site by 1, 2, 3, 4, 5 or more unmodified nucleotides.

10. The isolated oligonucleotide of claim 7, wherein two or more 2' modified nucleotides are contiguous.

11. The isolated oligonucleotide of claim 10, wherein the number of contiguous 2' modified nucleotides is 2, 3, 4, 5, or more.

12. The isolated oligonucleotide of claim 11, wherein 5 contiguous 2'-O-methyl modified nucleotides are positioned at the 5' end of the sequence complementary to the target nucleic acid molecule.

13. The isolated oligonucleotide of claim 7, wherein the nicking enzyme recognition sequence is 5'-GAGT-3'.

* * * * *